United States Patent
Chow et al.

(10) Patent No.: US 7,139,612 B2
(45) Date of Patent: Nov. 21, 2006

(54) MULTI-PHASIC MICROPHOTODIODE RETINAL IMPLANT AND ADAPTIVE IMAGING RETINAL STIMULATION SYSTEM

(75) Inventors: Vincent Chow, Hanover Park, IL (US); Alan Y. Chow, Wheaton, IL (US)

(73) Assignee: Optobionics Corporation, Naperville, IL (US)

( * ) Notice: Subject to any disclaimer, the term of this patent is extended or adjusted under 35 U.S.C. 154(b) by 267 days.

(21) Appl. No.: 10/600,404

(22) Filed: Jun. 20, 2003

(65) Prior Publication Data

US 2004/0088026 A1 May 6, 2004

Related U.S. Application Data

(63) Continuation of application No. 09/824,519, filed on Apr. 2, 2001, now Pat. No. 6,611,716, which is a continuation of application No. 09/100,336, filed on Mar. 26, 1998, now Pat. No. 6,230,057, which is a continuation of application No. 08/642,702, filed on Jun. 3, 1996, now abandoned, which is a continuation-in-part of application No. 08/465,766, filed on Jun. 6, 1995, now Pat. No. 5,895,415.

(51) Int. Cl.
*A61N 1/18* (2006.01)

(52) U.S. Cl. .............................. 607/53; 607/54; 607/1; 607/88; 623/4.1

(58) Field of Classification Search ................. 607/53, 607/56, 57, 1, 3, 88, 139, 141, 54; 345/8, 345/32; 623/4.1
See application file for complete search history.

(56) References Cited

U.S. PATENT DOCUMENTS 2,760,483 A   10/1956 Tassicker (Continued)

FOREIGN PATENT DOCUMENTS

DE   195 29 371 A1   2/1997

(Continued)

OTHER PUBLICATIONS

Article published in Science News, Feb. 2, 1974, vol. 105, No. 5, p. 105. Jerald Graeme, Photodiode Amplifiers OP Amp Solutions, Position-Sensing Photodiode Amplifiers—Chapter 10, published 1995.

(Continued)

*Primary Examiner*—Kennedy Schaetzle
(74) *Attorney, Agent, or Firm*—Vedder Price Kaufman & Kammholz

(57) ABSTRACT

An artificial retina device and a retinal stimulation system and method for stimulating and modulating its function is disclosed. The artificial retina device includes multi-phasic microphotodiode subunits. In persons suffering from blindness due to outer retinal layer damage, a plurality of such devices, when surgically implanted into the subretinal space, may allow useful formed artificial vision to develop. By projecting real or computer controlled visible light images, and computer controlled infrared light images or illumination, simultaneously or in rapid alternation onto the artificial retina device, the nature of induced retinal images may be modulated and improved. The retinal stimulation system may be worn as a headset. Color images may be induced by programming the stimulating pulse durations and frequencies of the stimulation.

21 Claims, 22 Drawing Sheets

U.S. PATENT DOCUMENTS

| | | | |
|---|---|---|---|
| 3,594,823 A | | 7/1971 | Collins |
| 3,628,193 A | | 12/1971 | Collins |
| 3,687,029 A | * | 8/1972 | Leczkowski ............... 396/61 |
| 3,724,932 A | * | 4/1973 | Cornsweet et al. ......... 351/210 |
| 3,766,311 A | | 10/1973 | Boll |
| 3,848,608 A | | 11/1974 | Leonard |
| 3,914,800 A | | 10/1975 | Collins |
| 4,001,867 A | | 1/1977 | Kravitz et al. |
| 4,145,122 A | * | 3/1979 | Rinard et al. ............... 351/210 |
| 4,211,474 A | | 7/1980 | Le Goff |
| 4,212,226 A | * | 7/1980 | Teltscher ................... 89/41.06 |
| 4,251,887 A | | 2/1981 | Anis |
| 4,272,910 A | | 6/1981 | Danz |
| 4,492,448 A | * | 1/1985 | Ishikawa et al. ............ 396/135 |
| 4,509,842 A | * | 4/1985 | Taniguchi et al. ............ 396/81 |
| 4,551,149 A | | 11/1985 | Sciarra |
| 4,600,004 A | | 7/1986 | Lopez et al. |
| 4,601,545 A | | 7/1986 | Kern |
| 4,628,933 A | | 12/1986 | Michelson |
| 4,679,572 A | | 7/1987 | Baker, Jr. |
| 4,707,595 A | * | 11/1987 | Meyers ................... 250/504 R |
| 4,750,498 A | | 6/1988 | Graham |
| 4,755,045 A | * | 7/1988 | Borah et al. ................. 351/210 |
| 4,810,050 A | | 3/1989 | Hooper |
| 4,836,202 A | | 6/1989 | Krasner |
| 4,873,448 A | | 10/1989 | Shirai |
| 4,978,842 A | | 12/1990 | Hinton et al. |
| 4,991,183 A | * | 2/1991 | Meyers ....................... 372/109 |
| 5,016,633 A | | 5/1991 | Chow |
| 5,024,223 A | | 6/1991 | Chow |
| 5,109,844 A | | 5/1992 | De Juan et al. |
| 5,130,528 A | | 7/1992 | Phillips, Jr. |
| 5,130,776 A | | 7/1992 | Popovic et al. |
| 5,159,927 A | | 11/1992 | Schmid |
| 5,223,728 A | | 6/1993 | Gempe |
| 5,254,852 A | | 10/1993 | Filipovich et al. |
| 5,256,882 A | | 10/1993 | Miyasaka |
| 5,338,991 A | | 8/1994 | Lu |
| 5,351,309 A | | 9/1994 | Lee et al. |
| 5,397,350 A | | 3/1995 | Chow et al. |
| 5,411,540 A | | 5/1995 | Edell et al. |
| 5,471,542 A | * | 11/1995 | Ragland ...................... 382/128 |
| 5,476,494 A | | 12/1995 | Edell et al. |
| 5,491,349 A | | 2/1996 | Komoto et al. |
| 5,495,364 A | * | 2/1996 | Palmer ........................ 359/412 |
| 5,556,423 A | | 9/1996 | Chow et al. |
| 5,648,655 A | | 7/1997 | Rostoker |
| 5,653,751 A | * | 8/1997 | Samiy et al. ............... 623/6.63 |
| 5,689,619 A | * | 11/1997 | Smyth ........................... 706/45 |
| 5,703,637 A | * | 12/1997 | Miyazaki et al. .............. 348/53 |
| 5,717,201 A | | 2/1998 | Lin et al. |
| 5,837,995 A | | 11/1998 | Chow et al. |
| 5,895,415 A | | 4/1999 | Chow et al. |
| 6,230,057 B1 | | 5/2001 | Chow et al. |
| 6,389,317 B1 | | 5/2002 | Chow et al. |

FOREIGN PATENT DOCUMENTS

| | | |
|---|---|---|
| EP | 0 084 621 | 8/1983 |
| EP | 0 233 789 | 8/1987 |
| EP | 0 460 320 A2 | 12/1991 |
| EP | 0 501 904 A2 | 9/1992 |
| GB | 2 016 276 A | 9/1979 |
| GB | 2 229 543 A | 9/1990 |
| WO | WO 96/17562 | 6/1996 |

OTHER PUBLICATIONS

Sze S.M. Textbook "Physics of Semiconductor Devices", Second Edition, John Wiley & Sons, pp. ix-xii, 32, 78, 415, 433, 749, 754-760, 790-791, 799-801, dated 1981.

Chapin, D.M. "A New Silicon p-n Junction Photocell for Converting Solar Radiation Into Electrical Power", Journal of Applied Physics, vol. 25, 1954, pp. 676-677.

Flynn, J.B. "Total Active Area Silicon Photo Diode Array", IEEE Transactions on Electron Devices, vol. ED-16, No. 10, Oct. 1969, pp. 877-879.

Ando, H. "Design Consideration and Performance Of A New MOS Imaging Device", IEEE Transactions On Electron Devices, vol. ED-32, No. 8, Aug. 1985, pp. 1484-1489.

Bergmann-Schaefer, Textbook "Lehrbuch Der Experimentalphysik", Walter de Gruyter, 1971, pp. 512-513 and translation.

Rosen, J.M. "A Merger Of Microsurgery And Microelectronics" in: Andrade J.D. et al. (Ed.), "Artificial Organs", VCH Publishers, 1967, pp. 583-594.

Encyclopedia of Electronics, 2.sup.nd Ed., 1990, pp. 640-642, 645.

The Photonics Design & Applications Handbook 1996, Book 3, "Detectors" Expanded Photodetector Choices Pose Challenges for Designers, pp. H-115-H-118.

Illingworth, The Penguin Dictionary of Electronics, 2.sup.nd Ed. 1988, pp. 410-413.

Lin et al., "The Vertical Intergration of Crystalline NMOS and Amorphous Orientational Edge Detector", IEEE Transactions on Electron Devices, vol. 39, No. 12, Dec. 1992.

Shannon, R.V. "A Model Of Safe Levels For Electrical Stimulation", IEEE Tarns Biomed Eng., 1992; 39:424-426.

Armington, J.C., Brigell, M. "Effects Of Stimulus Location And Pattern Upon The Visually Evoked Cortical Potential And The Electroretinogram", Int. J. Neurosci, 1981; 14:169-178.

Fenwick, P.B.C., Stone, S.A. Bushman, J., Enderby, D., "Changes In The Patter Reversal Visual Evoked Potential As A Function Of Inspired Nitrous Oxide Concentration", Electroencephalog Clin Neurophysiol, 1984; 57: 178-183.

Rovamo, J., Virsu, A., "An Estimation And Application Of The Human Cortical Magnification Factor", Exp Brain Res., 1979; 37:495-510.

Rovamo, J., Virsu, A., "An Estimation And Application Of The Human Cortical Magnification Factor", Exp Brain Res., 1979; 37:495-510.

Knighton R.W. "An Electrically Evoked Slow Potential Of The Frog's Retina. I. Properties Of Response", J. Neurophysiol, 1975; 38-185-197.

Brindley, G.S. "The Site Of Electrical Excitation Of The Human Eye", J. Physiol, 1955; 127-189-200.

Brindley G.S., "Beats Produced By Simultaneous Stimulation Of The Human Eye With Intermittent Light And Intermittent Or Alternating Electric Current", J. Physiol, 1962; 164:156-167.

Potts, AM, Inoue J., Buffum D., "The Electrically Evoked Response Of The Visual System (EER)", Invest Ophthalmol Vis Sci., 1968; 7:269-278.

Humayun M.S., Propst R.H., Hichingbotham, D., de Juan E. Jr., Dagnelie G., "Visual Sensations Produced By Electrical Stimulation Of The Retinal Surface In Patients With End-Stage Retenitis Pigmentosa (RP)", ARVO Abstracts, Invest Ophthalmol Vis. Sci., 1993; 34 (Suppl):835.

Tasman E., ed. Duane's Foundations of Clinical Ophthalmology, vol. 3, Philadelphia, Lippincott, 1992; chapter 13:20-25, chapter 50:1-12.

Stone J.L., Barlow, W.E., Humayun, M.S., de Juan E., Jr., Milam, A.H., "Morphometric Analysis Of Macular Photoreceptor And Ganglion Cells In Retinas Pigmentosa", Arch Ophthalmol, 1992; 110:1634-1639.

Pagon, R.A., "Retinitis Pigmentosa", Surv Ophthalmol., 1988, 33:137-177.3.

Eagle, R.C., Lucier, A.C., Bernardino, V.B., et al., "Retinal Pigment Epithelial Abnormalities In Fundus Flavimaculatus", Opthalmol, 1980; 87:1189-1200.

Article published in Science, Jul. 1981. Dowling, J.E., Ripps, H, "Visual Adaptation In The Retina Of The Skate", J Gen Physiol. 1970; 56:491-520.

Humayun, M., Propst R., De Juan, E., et al. "Bipolar Surface Electrical Stimulation Of The Vertebrate Retina", Arch Ophthalmol, 1994; 112:110-116.

Narayanan, M.V., Rizzo, J.F., Edell, D., et al. "Development Of A Silicon Retinal Implant: Cortical Evoked Potentials Following Focal Stimulation Of The Rabbit Retina With Light And Electricity", ARVO Abstracts, Invest Ophthalmol Vis Sci., 1994; 35(Suppl):1380.

Dawson, W.W., Radtke, N.D., "The Electrical Stimulation Of The Retina by Indwelling Electrodes", Invest Ophthalmol Vis Sci., 1977; 16:249-252.

Brady, G.S., Clauser, H.R., Materials Handbook, Thirteenth Edition, New York, McGraw-Hill, 1991; 739-740.

Paton, D., Goldberg, M.F., Management Of Ocular Injuries, Philadelphia, W.B. Saunders Co., 1976; 739-740.

Terr, L.I., Linthicum, F.H., House, W.F., "Histopathologic Study Of The Cochlear Nuclei After 10 Years Of Electrical Stimulation Of The Human Cochlea", Am J Otol., 1988; 9:1-7.

Agnew, W.F. McGreery, D.B. Neural Prostheses Fundamental Studies, Englewood Cliffs, Prentice Hall, 1990: 25-65.

Curcio, C.A., Sloan, K.R., Kaliha, R.E. Hendrickson, A.E., "Human Photoreceptor Topography", J of Comparative Neurology, 1990; 292:497-523.

Brown et al., "Monolithically Integrated 1 × 12 Array Of Planar InGaAs/InP Photodiodes", Journal of Lightwave Technology, vol. LT-4, No. 3, Mar. 1986, pp. 283-286.

Melen, et al. "A Transparent Electrode CCD Image Sensor For A Reading Aid For The Blind", IEEE Journal Of Solid-State Circuits, vol. sc-9, No. 2, Apr. 1974, pp. 41-68.

Kataoka, "An Attempt Towards An Artificial Retina: 3-D IC Technology For An Intelligent Image Sensor", Transducers '85: International Conference On Solid-State Sensors And Actuators 1985, pp. 440-442.

Hagins, W.A., Penn, R.D., Yoshikami, S. "Dark Current And Photocurrent in Retinal Rods", Biophys J., 1970; 10:380-412.

Tomita, T., "Electrical Activity Of Vertebrate Photoreceptor", Q Rev Biophys., 1970, 3:179-222.

Baylor, D.A., Fuortes, M.G.F., "Electrical Responses Of Single Cones In The Retina Of The Turtle", J Physiol, 1970, 207:77-92.

Chow, A.Y., "Electrical Stimulation Of The Rabbit Retina With Subretinal Electrodes And High Density Microphotodiode Array Implants", ARVO Abstracts, Invest Ophthalmol Vis Sci. 1993; 34 (Suppl):835.

Rubin, M.L., Optics for Clinicians, Gainsville, TRIAD Scientific Publishers, 1974; 119-123.

Boettner, E.A., Wolter, J.R. "Transmission Of The Ocular Media", Invest Ophthalmol, 1962; 1:776-783.

European Search Report dated Jun. 17, 2004 for European Application No. EP 04 00 8614.

\* cited by examiner

MULTI-PHASIC MICROPHOTODIODE RETINAL IMPLANT AND ADAPTIVE IMAGING RETINAL STIMULATION SYSTEM

This is a Continuation of U.S. patent application Ser. No. 09/824,519, filed Apr. 2, 2001, now U.S. Pat. No. 6,611,716 which is a Continuation of U.S. patent application Ser. No. 09/100,336, filed Mar. 26, 1998, now issued as U.S. Pat. No. 6,230,057, which is a Continuation of U.S. patent application Ser. No. 08/642,702, filed Jun. 3,1996, now abandoned, which is a Continuation-In-Part of U.S. patent application Ser. No. 08/465,766, filed Jun. 6, 1995, now issued as U.S. Pat. No. 5,895,415, which are incorporated by reference herein.

BACKGROUND OF THE INVENTION

The present invention is a medical product that can be used to correct vision loss or even complete blindness caused by certain retinal diseases. A variety of retinal diseases cause vision loss or blindness by destruction of the vascular layers of the eye including the choroid, choriocapillaris, and the outer retinal layers including Bruch's membrane and retinal pigment epithelium. Loss of these layers is followed by degeneration of the outer portion of the inner retina beginning with the photoreceptor layer. Variable sparing of the remaining inner retina composed of the outer nuclear, outer plexiform, inner nuclear, inner plexiform, ganglion cell and nerve fiber layers, may occur. The sparing of the inner retina allows electrical stimulation of this structure to produce sensations of light.

Prior efforts to produce vision by electrically stimulating various portions of the retina have been reported. One such attempt involved an externally powered photosensitive device with its photoactive surface and electrode surfaces on opposite sides. The device theoretically would stimulate the nerve fiber layer via direct placement upon this layer from the vitreous body side. The success of this device is unlikely due to it having to duplicate the complex frequency modulated neural signals of the nerve fiber layer. Furthermore, the nerve fiber layer runs in a general radial course with many layers of overlapping fibers from different portions of the retina. Selection of appropriate nerve fibers to stimulate to produce formed vision would be extremely difficult, if not impossible.

Another device involved a unit consisting of a supporting base onto which a photosensitive material such as selenium was coated. This device was designed to be inserted through an external scleral incision made at the posterior pole and would rest between the sclera and choroid, or between the choroid and retina. Light would cause a potential to develop on the photosensitive surface producing ions that would then theoretically migrate into the retina causing stimulation. However, because that device had no discrete surface structure to restrict the directional flow of charges, lateral migration and diffusion of charges would occur thereby preventing any acceptable resolution capability. Placement of that device between the sclera and choroid would also result in blockage of discrete ion migration to the photoreceptor and inner retinal layers. That was due to the presence of the choroid, choriocapillaris, Bruch's membrane and the retinal pigment epithelial layer all of which would block passage of those ions. Placement of the device between the choroid and the retina would still interpose Bruch's membrane and the retinal pigment epithelial layer in the pathway of discrete ion migration. As that device would be inserted into or through the highly vascular choroid of the posterior pole, subchoroidal, intraretinal and intraorbital hemorrhage would likely result along with disruption of blood flow to the posterior pole. One such device was reportedly constructed and implanted into a patient's eye resulting in light perception but not formed imagery.

A photovoltaic device artificial retina was also disclosed in U.S. Pat. No. 5,024,223. That device was inserted into the potential space within the retina itself. That space, called the subretinal space, is located between the outer and inner layers of the retina. The device was comprised of a plurality of so-called Surface Electrode Microphotodiodes ("SEMCPs") deposited on a single silicon crystal substrate. SEMCPs transduced light into small electric currents that stimulated overlying and surrounding inner retinal cells. Due to the solid substrate nature of the SEMCPs, blockage of nutrients from the choroid to the inner retina occurred. Even with fenestrations of various geometries, permeation of oxygen and biological substances was not optimal.

Another method for a photovoltaic artificial retina device was reported in U.S. Pat. No. 5,397,350, which is incorporated herein by reference. That device was comprised of a plurality of so-called Independent Surface Electrode Microphotodiodes (ISEMCPs), disposed within a liquid vehicle, also for placement into the subretinal space of the eye. Because of the open spaces between adjacent ISEMCPs, nutrients and oxygen flowed from the outer retina into the inner retinal layers nourishing those layers. In another embodiment of that device, each ISEMCP included an electrical capacitor layer and was called an ISEMCP-C. ISEMCP-Cs produced a limited opposite direction electrical current in darkness compared to in the light, to induce visual sensations more effectively, and to prevent electrolysis damage to the retina due to prolonged monophasic electrical current stimulation.

These previous devices (SEMCPs, ISEMCPs, and ISEMCP-Cs) depended upon light in the visual environment to power them. The ability of these devices to function in continuous low light environments was, therefore, limited. Alignment of ISEMCPs and ISEMCP-Cs in the subretinal space so that they would all face incident light was also difficult.

SUMMARY OF THE INVENTION

This invention is, among other things, a system that allows for implantation of microscopic implants into the diseased eye so that the system can function in continuous low light levels, and also produce improved perception of light and dark details. This invention has two basic components: (1) multi-phasic microphotodiode retinal implants ("MMRIs") of microscopic sizes that are implanted into the eye, and (2) an externally worn adaptive imaging retinal stimulation system ("AIRES") that, among other things, uses infrared light to stimulate the MMRIs to produce "dark current" in the retina during low light conditions, and to improve perception of light and dark details.

In its basic form, a MMRI of this invention has, depending upon its orientation, a PiN configuration where the P-side of the implant has light filter layer that permits visible light to pass, and where the N-side of the implant has a light filter that permits only infrared ("IR") light to pass, and preferably only selected wavelength(s) of IR light. In practice, a population of such MMRIs are implanted in the so-called "subretinal space" between the outer and inner retina in the eye such that, randomly, about half of them (i.e. the first subpopulation) will be oriented so that their P sides face light incident to the eye, and about the other half (i.e. the second subpopulation) will be oriented so that their N-sides face light incident to the eye.

In this location and orientation, the first subpopulation of MMRIs convert energy from incoming visible light into small electrical currents to stimulate the sensation of light in the eye to produce formed vision. In other words, the first subpopulation converts visible light to electrical current to stimulate the retina with "light currents" to induce the perception of visible light. The second subpopulation of MMRIs converts infrared light provided by AIRES into electrical currents to stimulate the retina with "dark currents" during low light conditions to induce the perception of darkness.

The adaptive imaging retinal stimulation system or AIRES is comprised of a projection and tracking optical system ("PTOS"), a neuro-net computer ("NNC"), an imaging CCD camera ("IMCCD"), and an input stylus pad ("ISP").

In one embodiment of this invention, each microscopic implant comprises plural paired MMRI subunits disposed together in a single flattened cubic unit. The microscopic implants are fabricated so that each MMRI member of each pair has its positive pole electrode on one of the flattened surfaces, and its negative pole electrode on the other flattened surface. Each MMRI member of each pair is disposed so that it is oriented in the opposite direction from the other MMRI member of the pair, the negative (N) electrode of the first MMRI pair member being on or close to the same surface as the positive (P) electrode of the second MMRI pair member, and the positive electrode of the first MMRI pair member being on or close to the same surface as the negative electrode of the second MMRI pair member. Each of the flattened sides of a single microscopic implant therefore, has at least one associated positive microphotodiode electrode from one MMRI and one negative microphotodiode electrode from another MMRI. This symmetry ensures that each such microscopic implant functions in exactly the same manner regardless of which of the flattened surfaces faces incident light. Multiple layer dielectric filters are disposed on the P surfaces and N surfaces of the M subunits to allow visible light (400 to 740 nm) to pass through to the P surfaces and infrared light (740–900 nm) to pass through to the N surfaces In this manner, the PiN configuration of each MMRI subunit responds to visible light while the NiP configuration responds to infrared light.

In a modification of this embodiment, a common electrode, on each side of the implant, connects the positive pole electrode of one MMRI member to the negative pole electrode of the second MMRI member on the same side.

In the preferred embodiment, the flattened microscopic implant structures typically have a thickness to width and depth ratio of 1:3 and have a preference to orient themselves, within the subretinal space, with one of their flattened photoactive surfaces positioned to accept incident light. The P and N electrodes of each MMRI subunit, and/or the common electrode connecting the P and N electrodes, are on or close to the microscopic implant's light sensitive surfaces. Electric currents produced by the PiN configuration will stimulate the sensation of "light" in the overlying and/or adjacent retinal cells, while electric currents produced by the NiP configuration will stimulate the sensation of "darkness" in the vicinity of those same cells.

The power for the "light currents" is derived from the visible spectrum of light from incoming images. The power for the "dark currents" is provided by superimposed infrared (JR) light and/or images projected into the eye by an external computer-controlled optical headset system. This external computer controlled headset projection system is the second component of the artificial retinal device of this invention and is called the Adaptive Imaging Retinal Stimulation System "AIRES".

AIRES is comprised of component sub-systems of: a Projection and Tracking Optical System (PTOS), a Neuro-Net Computer (NNC), an Imaging CCD Camera (IMCCD), and an Input Stylus Pad (ISP). During operation, AIRES "sees" and interprets details and characteristics of images via its own IMCCD and processes this information with its NNC. It then projects modulated infrared light and/or images, and visible light images if necessary into the eye to modify implant function. By the use of a partially reflective and transmissive mirror in the PTOS, AIRES projects IR and visible light/images that are superimposed over the visible spectrum images passing into the eye from the environment. Initially, AIRES will be programmed using "patient input" from an input device, such as a stylus pad, to "train" the NNC on how to modify implant function to produce accurate images. After training, AIRES will have an improved capability to modulate implant function with little additional patient assistance. The primary advantages of this MMRI plus AIRES combination system over the previous art is that the combined system can still function in low light environments and that "light" and "dark" currents may be finely tuned by AIRES to provide optimal images. The production of opposing light and dark currents will also decrease any damaging effects from electrolysis, and improve implant biocompatibility.

In the preferred embodiment, the AIRES PTOS headset is worn by the patient, and projects variable intensity IR and visible-light images and illumination into the eye, by using an IR and visible-light capable CRT (IRVCRT). These IR and visible-light images and illumination will modify the function of the MMRI subunits of the implant by modulating their current output. In darkness, IR illumination is the predominate power source and powers the MMRI NiP configuration to produce electric currents that will stimulating the visual sensation of darkness. However, the IR induced NiP current is modified by the PTOS through NNC control, based upon information provide by the PTOS's ambient light sensors and IMCCD. Under bright lighting conditions, a higher current will be induced in the MMRI PiN configuration by ambient light, and will offset a modulated lower MMRI NiP current. This produces a net perception of light. Because images in the normal environment have constantly changing light and dark qualities, the implants will also rapidly change their electrical outputs between "light currents" and "dark currents". Modulation of the implant "light current" can also be performed by the AIRES PTOS by projecting additional visible light images, superimposed over the ambient light images.

During operation, AIRES uses its NNC to process digitized images provided by its IMCCD. In the preferred embodiment, AIRES projects superimposed, real-time-video, visible and infrared images onto the retinal implants. These images may be displayed either simultaneously or in rapid succession from the IRVCRT. Alternatively, any appropriate display device such as a filtered active matrix LCD, LED display, or filtered plasma display may be used to produce the visible and IR light and images. AIRES controls the PTOS projected images by changing their wavelengths, intensity, duration, and pulse frequency. A patient input device (e.g. an Input Stylus Pad) is also interfaced with the NNC and allows the patient to modify the IR and visible light images produced by the PTOS headset.

This patient "feedback" is analyzed by the AIRES NNC, then compared with the computer processed images from the IMCCD, and the differences learned by the AIRES Neuro-Net software. After a teaching period, the NNC is able to automatically adjust the computer generated visible and IR images to improve image quality without assistance by the patient. By adjusting the stimulating frequency and duration of the PTOS IR and visible images, AIRES will also be able to stimulate the sensation of color in some patients. This is in a manner similar to color sensations induced in normal sighted persons, by using a spinning black and white Benham top, or by using frequency modulated black and white television monitors.

The MMRI and AIRES components of this invention differ from the previous art primarily in the following ways. Visible and infrared images and light are used to selectively modulate MMRI function. A MMRI can be stimulated with light from either of its two photoactive sides and produce localized stimulating electric current from both sides. The flattened shapes of the MMRIs allow preferential orientation of the devices toward incident light when disposed in the subretinal space. Using the AIRES system, electrical output from MMRIs can be programmed for individual patient needs. The design of the MMRIs also allows the alternative to use them to stimulate the nerve fiber layer, ganglion cell layer, or inner plexiform layer of retina from vitreous body side; or to use them to stimulate the remnant photoreceptor layer, bipolar cell layer, or the inner plexiform layer from the subretinal space, by reversing their polarities during fabrication. The biphasic nature of the electrical current output from MMRIs are also better tolerated biologically than the mostly monophasic nature of electrical stimulation of the previous art.

DERAILED DESCRIPTION OF THE PRESENTLY PREFERRED EMBODIMENTS

Figure 1:
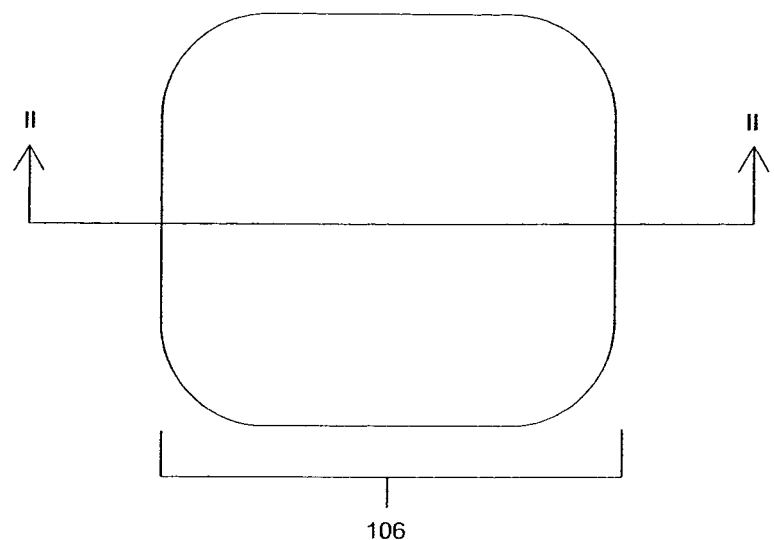
FIG. 1 is a plan view of one embodiment of the microphotodiode retinal implant of this invention (MMRI)

In a preferred embodiment of this invention (FIGS. 1–2), each microphotodiode implant (106) is fabricated as a flattened cubic device (hereafter MMRI) containing a single two-side microphotodiode. In this preferred embodiment, each MMRI (106) forms the shape of a flattened cube with rounded corners and edges, and is sized in microscopic dimensions, and is a physically independent unit MMRIs (106) may function as a PiN or NiP device, depending upon which of its two photosensitive sides, the P-side (107a) or the N-side (107b) is stimulated by visible and/or infrared light (108). From top to bottom, the layers of the MMRI (106) include the P electrode (110) preferably made of P doped polysilicon, a multilayer dielectric filter (122) to allow passage of only visible light (400 nm to 740 nm) to the next P+ layer (112), a contact pad (114) fabricated from any or all or compounds of the following: gold, aluminum, titanium, and chromium, to establish electrical contact between layers (110) and (112), an intrinsic layer (126) which forms naturally between the P+ layer (112) and the N-type silicon substrate (128), a N+ layer (118), a multilayer dielectric filter (124) to allow passage of only infrared light (740 nm to 900 nm) to the N+ layer (118), a contact pad (120) fabricated from any or all compounds of the following: gold, aluminum, titanium, and chromium to establish electrical contact between the N+ layer (118) and the last layer that is the N electrode (116), preferably made of N-doped polysilicon.

Figure 2:
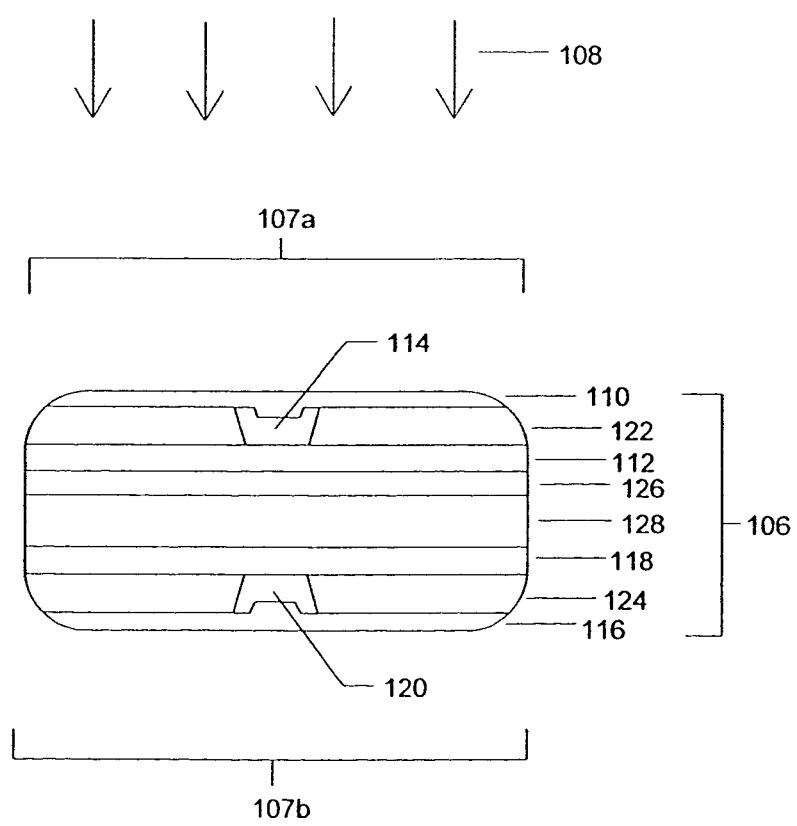
FIG. 2 is a cross-section taken along the plane of the line II—II of FIG. 1.

Although FIGS. 1–2 shows that the P electrode (110) and the N electrode (116) cover the entire surface of the MMRI (106), in alternate embodiments, the P electrode (110) may cover a fraction of the photosensitive side P-side (107a), and the N electrode (116) may cover a fraction of the photosensitive side N-side (107b). These fractions may range from 0.1% to 99.9%. The purpose of fractional coverage of the P electrode (110) and N electrode (116) is to allow concentration of electric currents produced by the MMRI (106). Also as shown in FIGS. 1–2, the width and depth of the MMRI (106) are the same dimensions and may vary between 5 µm and 100 µm, and the height is 25% to 50% that of the width and depth. However, in alternate embodiments, MMRIs (106) may be manufactured as small as 1 µm and as large as 2000 µm in depth and width, and the width and depth need not be the same; and the height of the MMRI may be from 1% to 500% of the width and depth. Preferably, the MMRI N-type silicon substrate (128) has an ohmic resistive value between 50 and 2000 ohm-cm2. However, in alternate embodiments, the MMRI N-type substrate (128) may have ohmic resistive values of between 1 ohm-cm2 and 100,000 ohm-cm2. The designed and preferred electric current output of each MMRI (106) is on the order of 1 to 5000 nA depending on incident lighting (108). Nevertheless, a range of 0.01 nA to 200,000 nA is also suitable.

Figure 3:
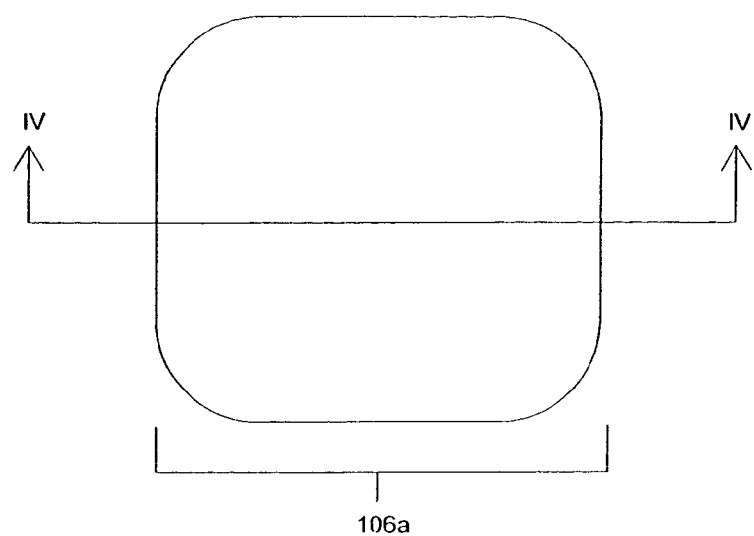
FIG. 3 is a plan view of a second embodiment of this invention MMRI-E)
Figure 4:
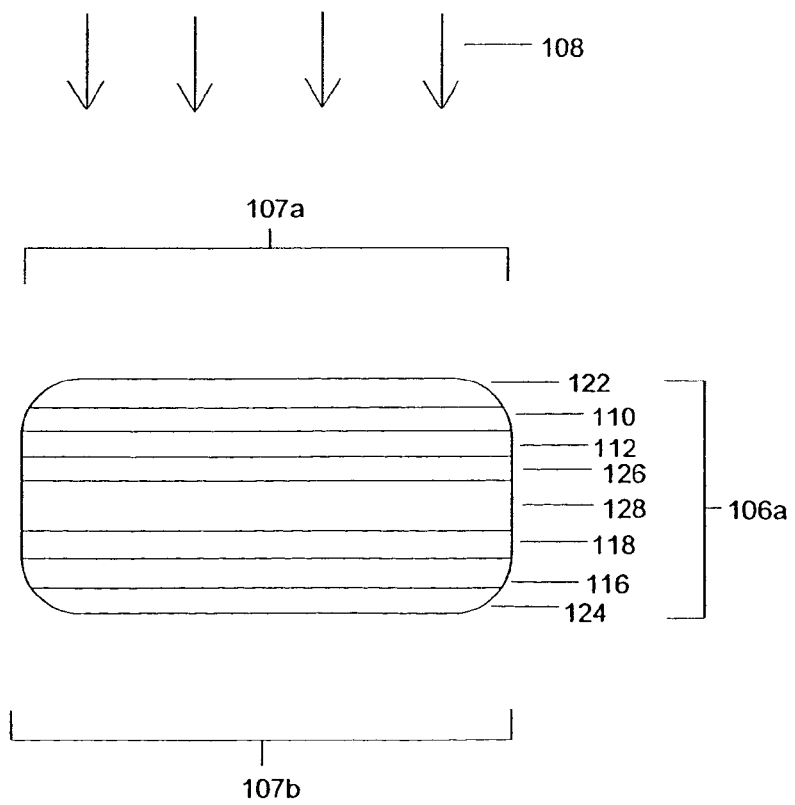
FIG. 4 is a cross-section taken along the plane of the line IV—IV of FIG. 3.

In a second embodiment of this invention (MMRI-E) (FIG. 3–4), the MMRIs of FIGS. 1–2 are fabricated so that the polysilicon layer 110 is sandwiched between the multilayer dielectric visible light filter layer 122 and the P+ layer 112, and the polysilicon layer 116 is sandwiched between the multi-layer dielectric IR filter layer 124 and the N+ layer 124. The aluminum contact pads 114 and 120 of FIGS. 1–2 are not be needed in this embodiment. This embodiment results in MMRI-Es which predominately stimulated retinal cells adjacent to the MMRI-Es rather than on top of the MMRI-Es. This second embodiment is used in those patients where side simulation will induce better vision than top stimulation. The remaining layers of the intrinsic layer 126, and the N-type silicon substrate layer 128, the P-side 107a, and the N-side 107b are unchanged.

Figure 5:
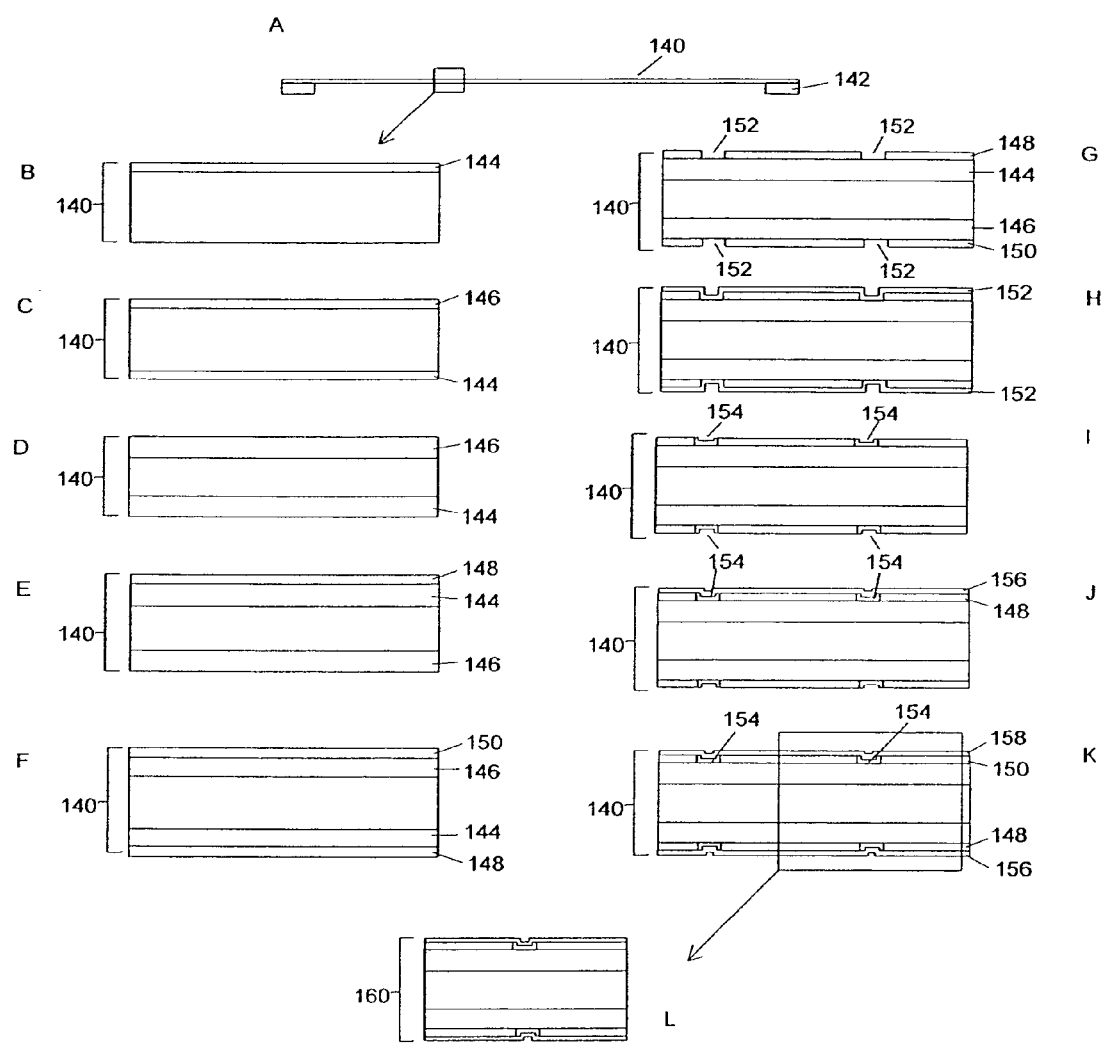
FIG. 5 shows the manufacturing process of the microphotodiode retinal implant of FIG. 1 (MMRI)

FIG. 5, A through L illustrates the manufacturing steps of the preferred MMRIs. As shown in FIG. 5A, a 3" float zone 1-0-0 N-type silicon wafer (140) at 200 to 400 ohm-cm is thinned to 8 µm, and a silicon support ring (142) 0.4" to 0.5" wide (prepared by chemical etch and channel stop techniques to have 30–40 degree i.d. taper) is then oxide bonded to target wafer (140). As shown in FIG. 5B, P+ layer (144) is ion implanted to 0.2 µm depth on one side of the wafer (140). The other side is masked from the implantation. As shown in FIG. 5C, wafer (140) is flipped over and the N+ layer (146) is ion implanted to 0.2 µm depth on the second side. The first P+ side (144) is masked from implantation.

As shown in FIG. 5D, both the P+ (144) and N+ (146) layers are thermally driven to 0.5 µm to 0.6 µm depth. As shown in 5E, Multiple alternating layers of TiO$_2$ and quartz are evaporation deposited to produce an interference filter (148) to pass 400–740 nm visible light, but stops 740 900 nm IR light on the P+ side (144). The total thickness of this dielectric layer (148) is about 3.5 to 5 µm. As shown in FIG. 5F, the wafer is flipped over to expose the N+ side (146) and multiple alternating layers of TiO$_2$ are evaporation deposited to produce a interference filter (150) which passes 740 900 nm IR light, but stops 400–740 nm visible light on the N+ side (146). Total thickness of this dielectric layer (150) is about 2–3 µm. In FIG. 5G, photoresist is spun-on and both sides of the wafer (140) are patterned with 8 µm×8 µm contact holes (152) which penetrate the interference films (148 and 150) to the P+ layer (144) and the N+ layer (146), with hole spacing of 50 µm in a square grid fashion. As shown in FIG. 5H, 1.0 µm of aluminum (152) is deposited to both sides of the wafer (140). In FIG. 5I, photoresist is spun-on and both sides of the wafer (140) are patterned to leave 12 µm×12 µm aluminum contact pads (154) over all the 8 µm×8 µm contact holes, and then thermally drive in the aluminum. In FIG. 5J, plasma assisted, low pressure, chemical vapor deposition is used to deposit 0.2 µm to 0.5 µm of P+ polysilicon (156) on the P+ side interference filter (148) of the wafer (140) to establish electrical contact with the aluminum contact pads (154), at 250°300° C. The other side of wafer is masked. In FIG. 5K, plasma assist, low pressure, chemical vapor is used to deposit 0.2 µm to 0.5 µm of N+ polysilicon (158) on N+ side interference filter (150) of the wafer (140) to establish electrical contact with the aluminum contact pads (154), at 250°300° C. The other side of wafer is masked. In FIG. 5L, the 3 inch wafer is eximer laser cut into 50 µm×50 µm squares (160) with one contact pad centered on each side of every square. The final cleaned, washed, and recovered squares are MMRIs. The MMRIs may be briefly tumbled in a glass container using ultrasonic energy to slightly round off the sharp corners and edges of the devices.

Figure 6:
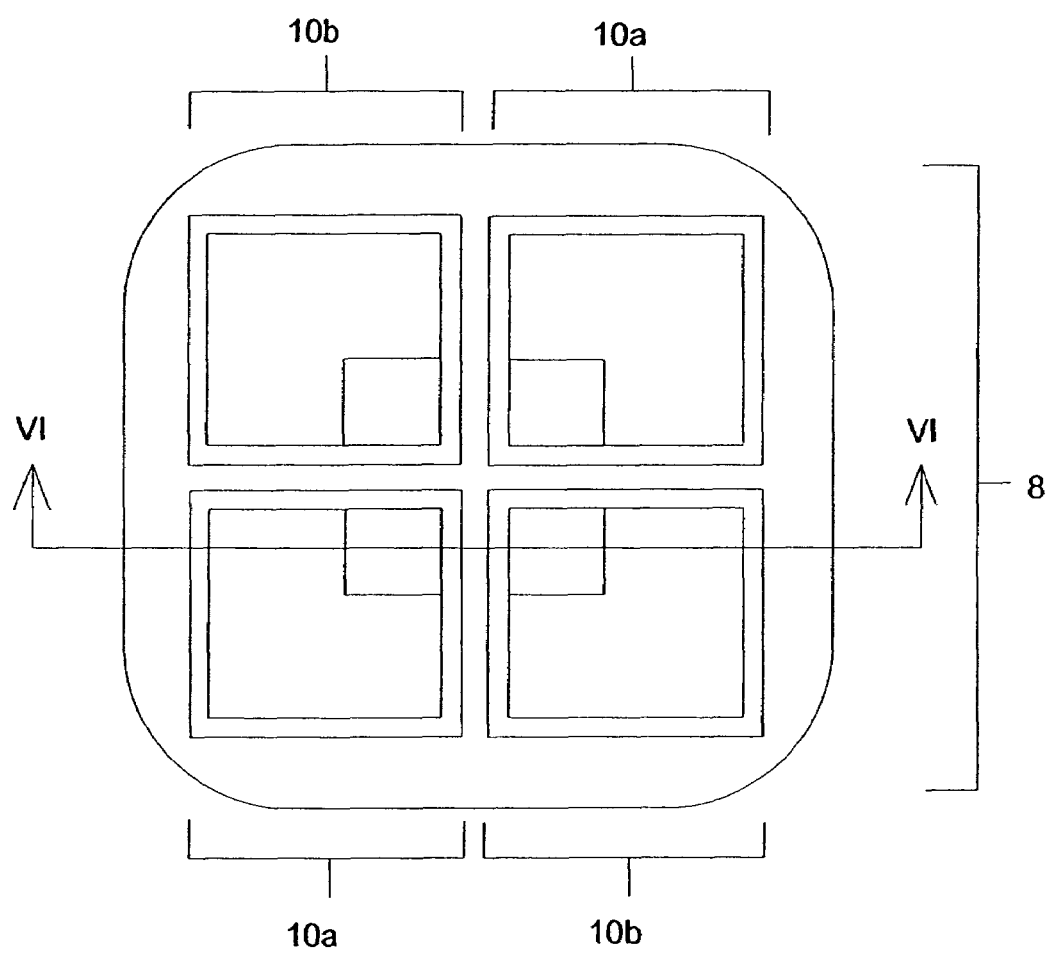
FIG. 6 is a plan view of a third embodiment of this invention (MMRI-4), which is composed of two pairs of MMRI subunits.
Figure 7:
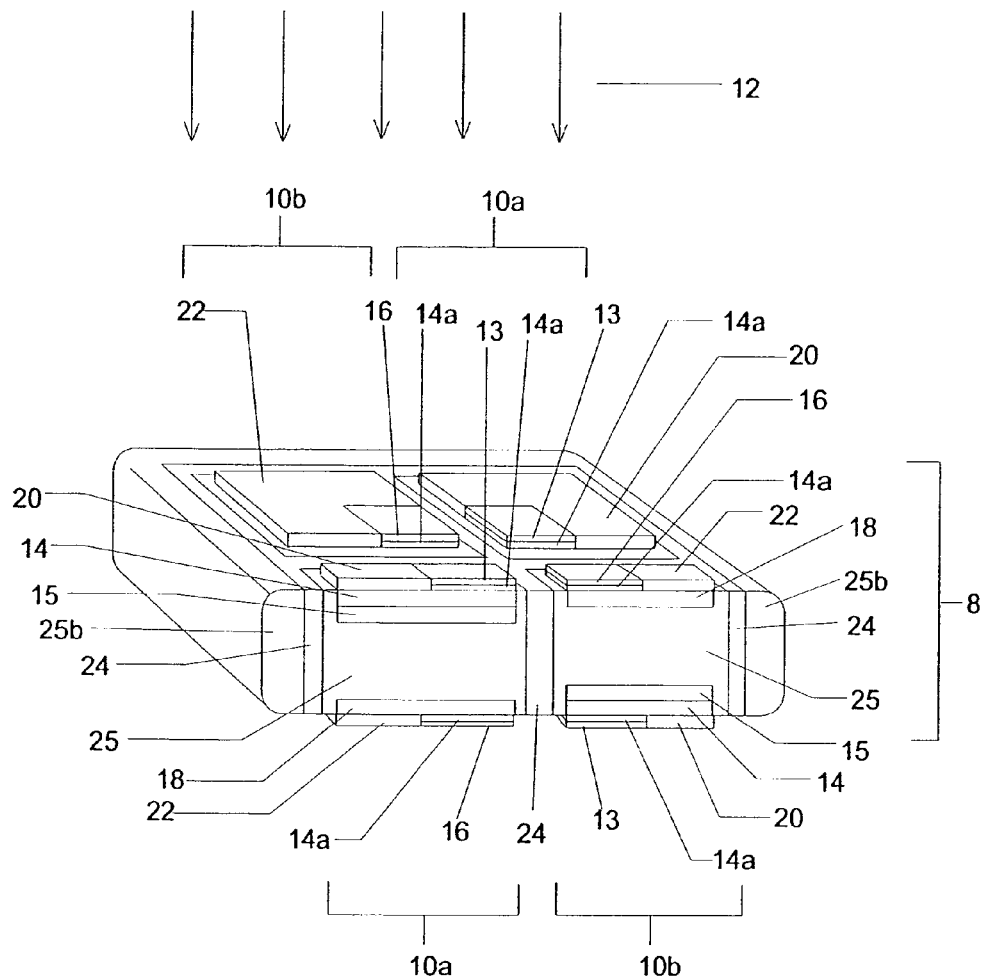
FIG. 7 is a perspective view in cross-section taken along the plane of line VI—VI of FIG. 6.

FIGS. 6–7 illustrate the layered microarchitecture of a third embodiment of the artificial retina device of this invention, designated at (8), and is referred to for convenience as a MMRI-4 to distinguish it from other embodiments of this invention. MMRI-4 (8) forms the shape of a flattened cube with rounded corners and edges, and is sized in microscopic dimensions. It is comprised of four microphotodiode subunits (10a×2 and 10b×2). Each microphotodiode subunit (10a or 10b) of the MMRI-4 (8) may be a PiN or NiP device, depending upon which of its photosensitive surfaces is oriented toward light (12). For example, as shown in FIG. 7, the near left microphotodiode (10a) is behaving as a PiN subunit, because the P+ tub (14) is facing incident light (12). In contrast, the near right microphotodiode (10b) is behaving as a NiP subunit because its N+ tub (18) is facing incident light (12). It can be readily appreciated, that if the MMRI-4 (8) is flipped over, the microphotodiode subunit (10a) will have its N+ tub (18) facing incident light and will therefore behave as a NiP device. Similarly, when flipped over, the microphotodiode subunit (10b) will have a P tub (14) facing incident light and will behave as a PiN device.

Further illustrated in FIGS. 6–7, the MMRI-4 (8) in its basic form contains four positive (P) electrodes (13) disposed on the four P+ tub (14) surfaces on the top and bottom sides of the MMRI-4 (8) (note the bottom structure of the two rear microphotodiode subunits cannot be seen in FIG. 7) The P electrodes (13) are preferably made of P doped polysilicon, produced by chemical vapor deposition, and are deposited on the inner corners of the P+ tubs (14). Interposed between the P electrodes (13) and the P+ tubs (14), is a layer of gold, titanium or chromium (14a) to promote adhesion and to act as a light block. The MMRI-4 (8) also contains four negative (N) electrodes (16) disposed on the four N+ tub (18) surfaces. The N electrodes (16) are preferably made of N-doped polysilicon, produced by chemical vapor deposition, and are deposited on the inner corners of the N+ tubs (18). Interposed between the N electrodes (16) and the N+ tubs (18) is also a layer of gold, titanium or chromium (14a) to promote adhesion and to act as a light block.

Alternatively, the P electrodes (13), and N electrodes (16) may be constructed of any suitable material that will conduct electric current. These conductive materials may include, but are not limited to, gold, chromium, aluminum, iridium, and platinum or any combination or compounds made from these materials. The P electrodes (13) and the N electrodes (16) may cover any fraction, from 0.1% to 99.9%, of their respective P+ tub (14) or N+ tub (18) surfaces. Filter layers (20) are disposed on the portion of the P+ tub (14) surfaces not covered by the P electrodes (13). These filter layers (20) are preferably fabricated from multi-layer dielectric coatings and allow passage of only visible light (400 nm to 740 nm) to the P+ tub (14) surfaces. Filter layers (22) are disposed on the N+ tub (18) surfaces not covered by the N electrodes (16). These filter layers (22), are also preferably fabricated from multi-layer dielectric coatings and allow passage of only infrared light (740 to 900 nm) to the N+ tub (18) surfaces. Under each P+ tub (14), an intrinsic layer (15) forms naturally between the P+ tub (14) and the N-type silicon substrate (25). The N+ tub layers (18) are created by ion implantation of additional N-type phosphorus into the N-type silicon substrate (25). Ion implantation of P-type boron around each MMRI-4 subunit (10a×2, 10b×2) produces a channel stop (24) to electrically separate the microphotodiode subunits from each other. Outside the channel stop material (24) is surrounding N-type silicon substrate (25b).

In the embodiment of the invention shown in FIGS. 6–7, the width and depth of the MMRI-4 (8) are the same dimensions and are between 10 and 50 microns, and the height is 25% to 50% that of the width and depth. This flattened cubic configuration will allow one or the other of the two flattened photoactive sides of the MMRI-4 (8) to be preferentially directed to incident light (12), when the MMRI-4 (8) is implanted in the subretinal space. MMRI-4s (8) may be manufactured as small as 1 micron and as large as 1000 microns in depth and width, and the width and depth need not be the same; further the height of the MMRI-4 may be from 1% to 500% of the width and depth. In the embodiment of FIGS. 6–7, the MMRI-4 N type substrate (25 and 25b) has an ohmic resistive value between 50 and 2000 ohm-cm$^2$. However, the MMRI-4 N-type substrate (25 and 25b I may have ohmic resistive values of between 1 ohm-cm$^2$ and 100,000 ohm-cm$^2$. The designed and preferred electric current output of each MMRI-4 subunit microphotodiode (10a or 10b) is on the order of 1 to 5000 nA depending on incident lighting (12). Nevertheless, a range of 0.01 nA to 200,000 nA may also be suitable. The MMRI-4 (8) may also be modified to achieve greater or lesser electrical output by changing the area of each P electrode (13), and/or the N electrode (16) relative to the area of their respective P+ tub (14) and N+ tub (18).

Figure 8:
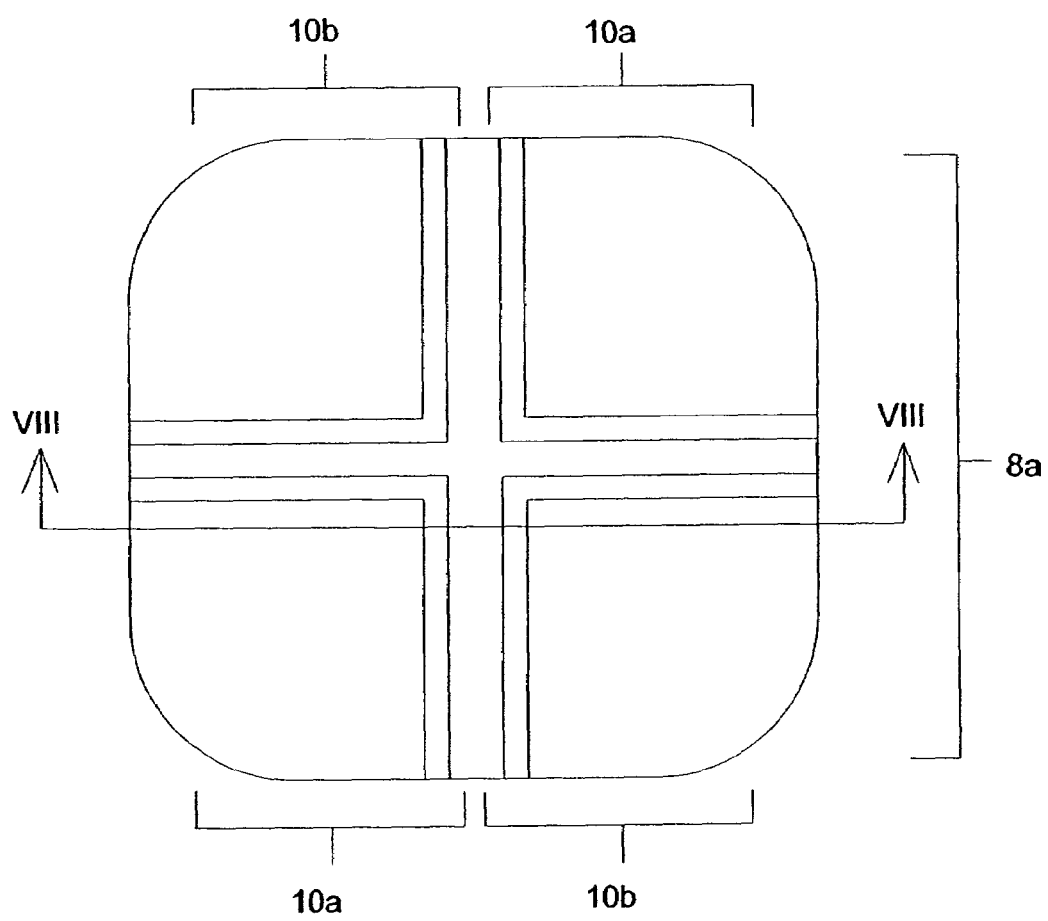
FIG. 8 is a plan view of a fourth embodiment of this invention (MMRI-4E), which is composed of two pairs of MMRI-E subunits.
Figure 9:
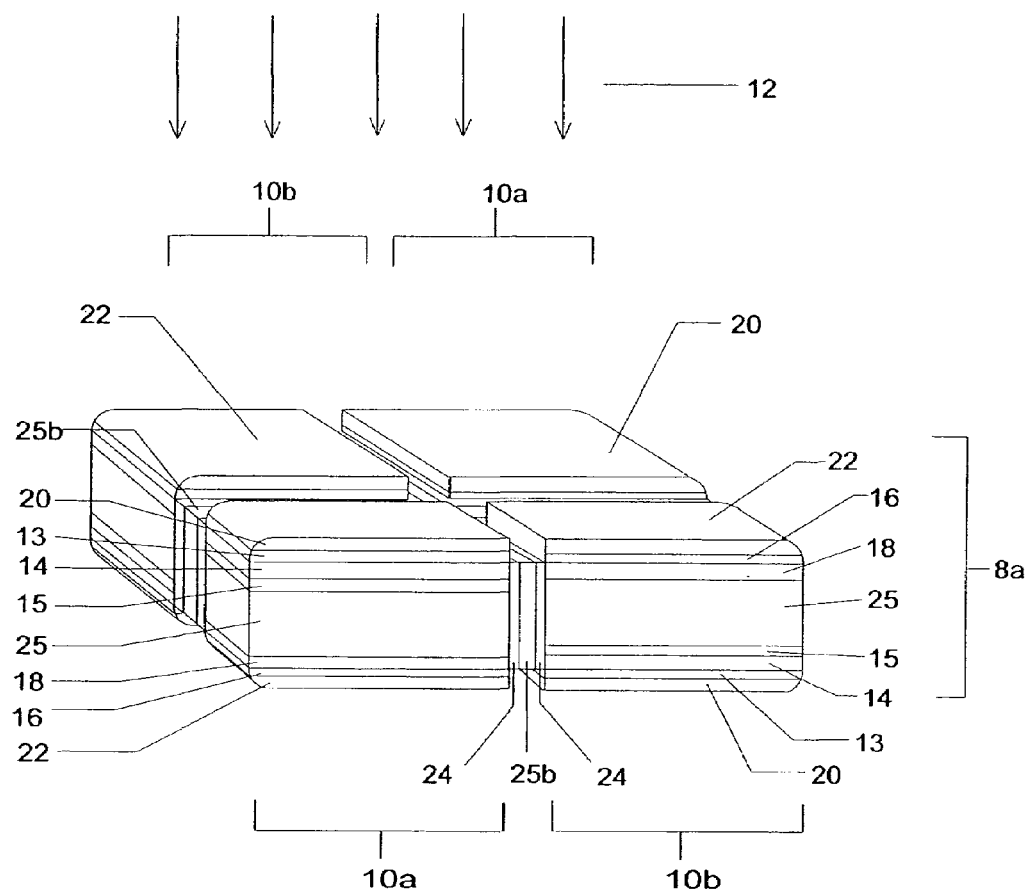
FIG. 9 is a perspective view in cross-section taken along the plane of line VIII—VIII of FIG. 8.

FIGS. 8–9 illustrate the layered microarchitecture of a fourth embodiment of the artificial retina device of this invention, designated at (8a), and is referred to for convenience as a MMRI-4E to distinguish it from other embodiments of this invention. MMRI-4E (8a) forms the shape of a flattened cube with rounded corners and edges, and is sized in microscopic dimensions. It is comprised of four microphotodiode subunits (10a×2 and 10b×2). Each microphotodiode subunit (10a or 10b) of the MMRI-4E (8a) may be a PiN or NiP device, depending upon which of its photosensitive surfaces is oriented toward light (12). For example, as shown in FIG. 9, the near left microphotodiode (10a) is behaving as a PiN subunit, because the P+ tub (14) is facing incident light (12). In contrast, the near right microphotodiode (10b) is behaving as a NiP subunit because its N+ tub (18) is facing incident light (12). It can be readily appreciated, that if the MMRI-4E (8a) is flipped over, the microphotodiode subunit (10a) will have its N+ tub (18) facing incident light and will therefore behave as a NiP device. Similarly, when flipped over, the microphotodiode subunit (10b) will have a P+ tub (14) facing incident light and will behave as a PiN device.

Further illustrated in FIGS. 8–9, the MMRI-4E (8a) in its basic form contains four transparent positive (P) electrodes (13) disposed on the four P+ tub (14) surfaces on the top and bottom sides of the MMRI-4E (8a) (note the bottom structure of the two rear microphotodiode subunits cannot be seen in FIG. 9). The transparent P electrodes (13) are preferably made of P doped polysilicon, produced by chemical vapor deposition, and are deposited on the P+ tubs (14). The MMRI-4E (8a) also contains four transparent negative (N) electrodes (16) disposed on the four N+ tub (18) surfaces. The transparent N electrodes (16) are preferably made of N-doped polysilicon, produced by chemical vapor deposition, and are deposited on the N+ tubs (18).

Alternatively, the P electrodes (13), and N electrodes (16) may be constructed of any suitable material that can be deposited in a thin transparent layer, and that will conduct electric current. These conductive materials may include, but are not limited to, gold, chromium, aluminum, iridium, and platinum or any combination or compounds made from these materials. Filter layers (20) are disposed on the P electrodes (13). These filter layers (20) are preferably fabricated from multi-layer dielectric coatings and allow passage of only visible light (400 nm to 740 nm) through to the transparent P electrodes (13) and then to the P+ tub (14) surfaces. Filter layers (22) are disposed on the N+ tub (18) surfaces. These filter layers (22), are also preferably fabricated from multi-layer dielectric coatings and allow passage of only infrared light (740 to 900 nm) through to the transparent N electrodes (16) and then to the N+ tub (18) surfaces. Under each P+ tub (14), an intrinsic layer (15) forms naturally between the P+ tub (14) and the N-type silicon substrate (25). The N+ tub layers (18) are created by ion implantation of additional N-type phosphorus into the N-type silicon substrate (25). Ion implantation of P-type boron around each MMRI-4 subunit (10a×2, 10b×2) produces a channel stop (24) to electrically separate the microphotodiode subunits from each other. Outside the channel stop material (24) is surrounding N-type silicon substrate (25b).

In the embodiment of the invention shown in FIGS. 8–9, the width and depth of the MMRI-4E (8a) are the same dimensions and are between 10 and 50 microns, and the height is 25% to 50% that of the width and depth. This flattened cubic configuration will allow one or the other of the two flattened photoactive sides of the MMRI-4E (8a) to be preferentially directed to incident light (12), when the MMRI-4E (8a) is implanted in the subretinal space. MMRI-4Es (8a) may be manufactured as small as 1 micron and as large as 1000 microns in depth and width, and the width and depth need not be the same; further the height of the MMRI-4E may be from 1% to 500% of the width and depth. In the embodiment of FIGS. 8–9, the MMRI-4E N type substrate (25 and 25b) has an ohmic resistive value between 50 and 2000 ohm-cm². However, the MMRI-4E N-type substrate (25 and 25b) may have ohmic resistive values of between 1 ohm-cm² and 100,000 ohm-cm². The designed and preferred electric current output of each MMRI-4E subunit microphotodiode (10a or 10b) is on the order of 1 to 5000 nA depending on incident lighting (12). Nevertheless, a range of 0.01 nA to 200,000 nA may also be suitable. The MMRI-4E (8a) may also be modified to achieve greater or lesser electrical output by changing the thickness and therefore the transparency of each P electrode (13), and/or the N electrode (16).

Figure 10:
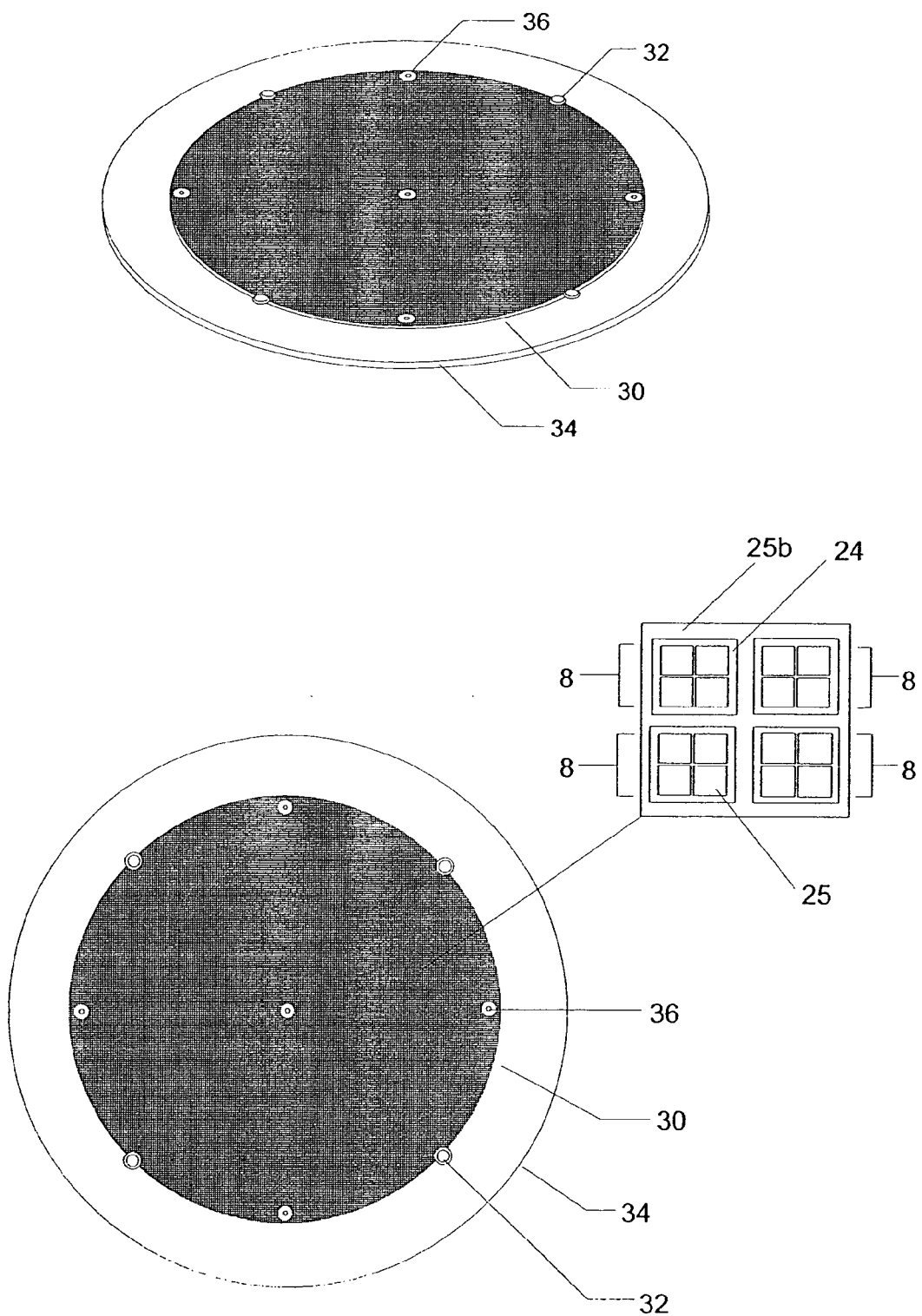
FIG. 10 shows three dimensional and plan views, and a magnified inset view of a 3 inch silicon wafer secured onto a thicker 4 inch silicon wafer during the manufacture of the microphotodiode retinal implants (MMRI-4) of FIG. 6.

In FIG. 10, and FIG. 10 inset, the manufacture of the preferred MMRI-4s (8) is illustrated. The first stage in the manufacture of MMRI-4s begins with a three-inch diameter N type 1-0-0 silicon wafer (30) that is 8 microns thick. This wafer (30) is secured around its circumference to a four-inch wafer (34) approximately 500 microns thick, with titanium pins (32). As shown in the FIG. 10 inset, a plurality of N-type square island groups (8) that eventually become the MMRI-4s are isolated from the surrounding N-type substrate (25b) by ion implantation of P-type boron channel stops (24) from both sides. The channel stops (24) are heat driven through the entire thickness of the three-inch diameter wafer (30) to isolate four square columns of N-type silicon substrate (25) per square island (8). Each square column (25) is 11 microns per side and separated from adjacent square columns (25) of the same MMRI-4 (8) by 1 micron of P-type silicon channel stop (24). The resultant square islands (8), including the channel stops (24) are 21 microns per side. The square islands (8) are separated from each other by 1 micron of N-type silicon substrate (25b). Alignment holes (36) are excimer laser drilled through the three-inch wafer (30). These holes (36) facilitate alignment of fabrication masks from either side of the three-inch wafer (30).

The P+ tubs (14) shown in FIG. 7 are created by ion implantation and thermal diffusion of P-type boron into the N-type substrate square columns (25). Two P+ tubs (14) are formed on each side of the MMRI-4 square island (8) and are arranged diagonally to each other. Intrinsic layers (15) automatically form between the P+ tubs (14) and the N type silicon substrate of the square columns (25). The N+ tubs (18) are created by ion implantation and thermal diffusion of additional N-type phosphorus into the N-type silicon substrate square columns (25) from the opposite side of the P+ tubs (14). After deposition of a gold, chromium or titanium layer (14a) to improve adhesion and to act as a light block on the inner corners of all the P+ tubs (14) and N+ tubs (18), P-doped polysilicon electrodes (13) and the N-doped polysilicon electrodes (16), each covering 10% of the P+ tub (14) and N+ tub (18) surfaces are then deposited on their respective P+ tubs (14) and N+ tubs (18). The three-inch wafer (30), still secured on the four-inch support wafer (34), of FIG. 10 is then transferred to a vacuum deposition chamber where multilayer dielectric coatings (20), that bandwidth pass visible light (400–740 nm) are deposited on the P+ tubs (14) and multilayer dielectric coatings (22) that bandwidth pass infrared light are deposited on the N+ tubs (18). The three-inch wafer (30) is then flipped over and re-secured on the four-inch support wafer (34). Again, multilayer dielectric coatings (20) that bandwidth pass visible light (400 to 740 nm), and multilayer dielectric coatings (22) that bandwidth pass infrared light (740 to 900 nm) are deposited on their respective P+ tubs (14) and the N+ tubs (18) after deposition of the gold, chromium or titanium adhesion and light block layer (14a).

As shown in FIG. 10, the final three-inch wafer (30), with fabricated MMRI-4 square islands (8), is then removed from the four-inch support wafer (34). The three-inch wafer (30) is then rebonded to the four-inch wafer (34) with an aqueous dissolvable adhesive. Using an excimer laser, X and Y direction cuts are made to separate the MMRI-4 islands (8) from each other. The MMRI-4 islands (8), however, still remain bonded to the support wafer (34) by adhesive. The wafer assembly (30 and 34) is then placed in an aqueous solution solvent to dissolve the adhesive. The MMRI-4 square islands (8) are recover from the aqueous solution using standard filtering techniques, and are washed and dried. The recovered MMRI-4 islands (8) are briefly tumbled in a glass container using ultrasonic energy. This tumbling process will slightly round off the sharp corners and edges of the MMRI-4s (8). The final devices, demonstrated by the MMRI-4s (8) of FIG. 7, are then washed again, recovered, sterilized, and then placed in a biologically compatible semisolid or liquid vehicle for implantation into the eye.

Figure 11:
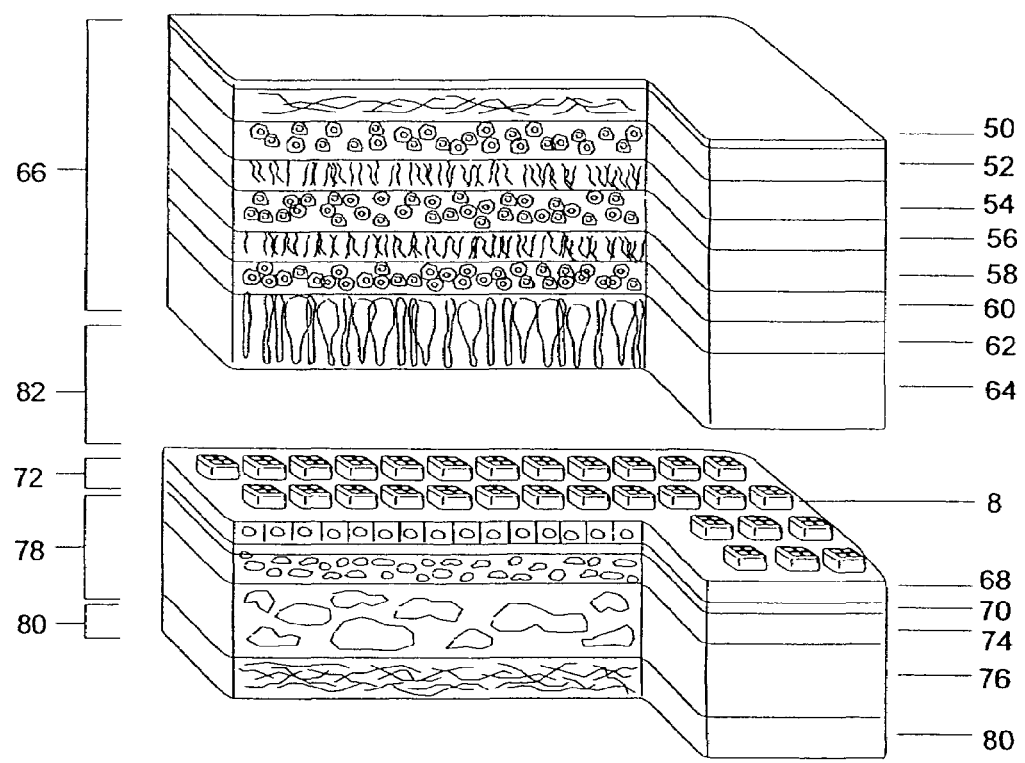
FIG. 11 shows the microphotodiode retinal implants (MMRI-4) of FIG. 6 implanted in the preferred location of the subretinal space.

FIG. 11 shows MMRI-4s (8) implanted in their preferred monolayer position in the subretinal space (82). The layers of the eye at the posterior pole from inside the eye to outside the eye are shown in their respective positions: internal limiting membrane (50); nerve fiber layer (52); ganglion and cell layer (54); inner plexiform layer (56); inner nuclear layer (58); outer plexiform layer (60); outer nuclear cell layer (62); and photoreceptor layer (64), all of which constitute the inner retinal layer (66). The MMRI-4s (8) are disposed between the inner retinal layer (66), and the retinal pigment epithelium (68) and Bruch's membrane (70), which together constitute the outer retinal layer (72). External to the outer retinal layer (72) are the choriocapillaris (74) and choroid (76) which comprise the choroidal vasculature (78), and sclera (80), which comprised the outer coat of the eye.

Figure 12:
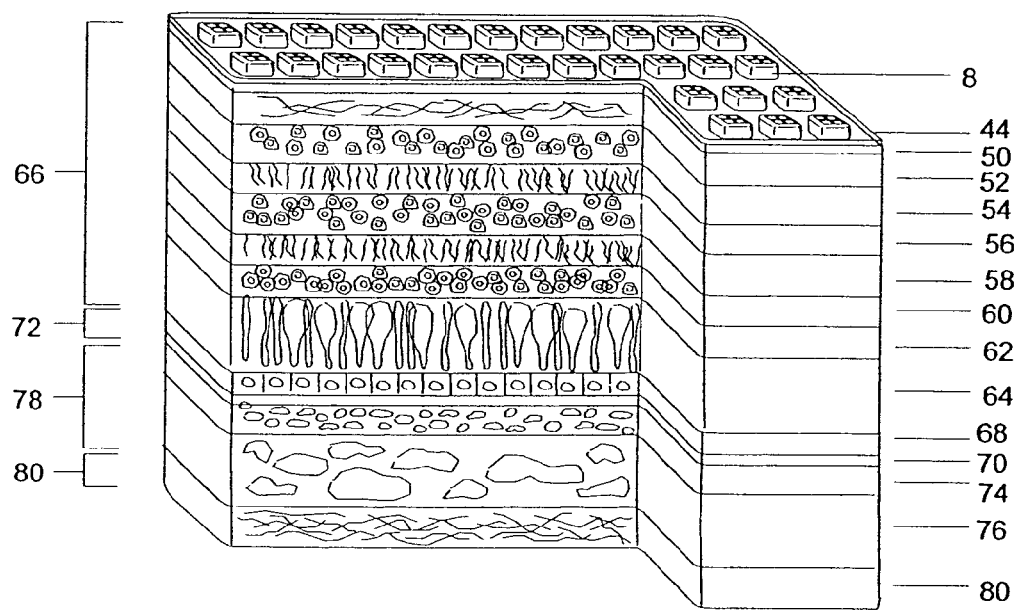
FIG. 12 shows the microphotodiode retinal implants (MMRI-4) of FIG. 6 implanted in an alternate location, on the nerve fiber layer surface of the retina.

FIG. 12 shows MMRI-4s (8) in an alternate embodiment location, positioned on the internal limiting membrane surface (50) of the retina and close to the nerve fiber layer (52). In this location, MMRI-4s (8) are embedded into a flexible, biologically compatible sheet (44), that allows both of the flattened photoactive surfaces of each MMRI-4s (8) to be exposed. Electrical stimulation of the retinal nerve fiber layer (52), through the internal limiting membrane surface (50) by the MMRI-4s (8) will also induce artificial vision, but the quality of images produced will not be as well formed as from stimulation of the retina from the subretinal space (82) as shown in FIG. 11. The layers of the eye at the posterior pole from inside the eye to outside the eye, shown in their respective positions in FIG. 12, are: internal limiting membrane (50); nerve fiber layer (52); ganglion cell layer (54); inner plexiform layer (56); inner nuclear layer (58); outer plexiform layer (60); outer nuclear layer (62); and photoreceptor layer (64), all of which constitute the inner retinal layer (66). The retinal pigment epithelium (68) and Bruch's membrane (70), together constitute the outer retinal layer (72). External to the outer retinal layer (72), choriocapillaris (74) and choroid (76) comprise the choroidal vasculature (78), and sclera (80), the outer coat of the eye.

As illustrated in FIGS. 13–16, in a further embodiment of the MMRI component of this invention, the two dielectric filter layers embedded in each MMRI will be both of the visible light transmitting type (210, 222), or will be both of the IR light transmitting type (310, 322). Instead of using polysilicon for their electrodes, the electrodes of these devices (202, 204, 302, 304) may be fabricated from gold, although aluminum or platinum may also be used, and will be deposited with an industry standard "wafer bumping" process. This will form each electrode into a projecting-like structure bonded to an aluminum contact pad (214, 224, 314, 324). Each gold projecting electrode (202, 204, 302, 304) will be then covered over its entire surface, with the exception of the tip, by an insulating layer of silicon dioxide (208, 226, 308, 326) or alternatively silicon nitride. The height of the projecting electrode will be higher on one side of the device than on the other side, and may be 5 µm to 200 µm on the higher side (202, 302) and 1 µm to 195 ~m on the lower side (204, 304). When thus fabricated, these individual devices are will form two populations: (1) a visible light responsive device ("MMRI-IPV") designated at (200) with a higher projecting electrode (HPE) (202) on the negative (N) side (205b), and a lower projecting electrode (LPE) (204) on the positive (P) side (205a), and (2) a IR light responsive device ("MMRI-IPIR") designated at (300) with a HPE (302) on the P side (305b) and a LPE (304) on the N side (305a).

Figure 17:
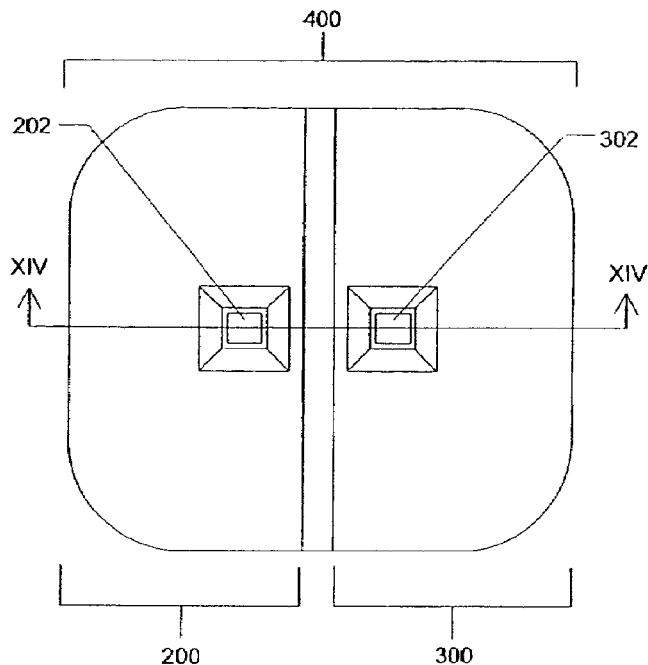
FIG. 17 shows a plan view of a seventh embodiment of the microphotodiode implant of this invention (MMRI-IPVIR-A)
Figure 18:
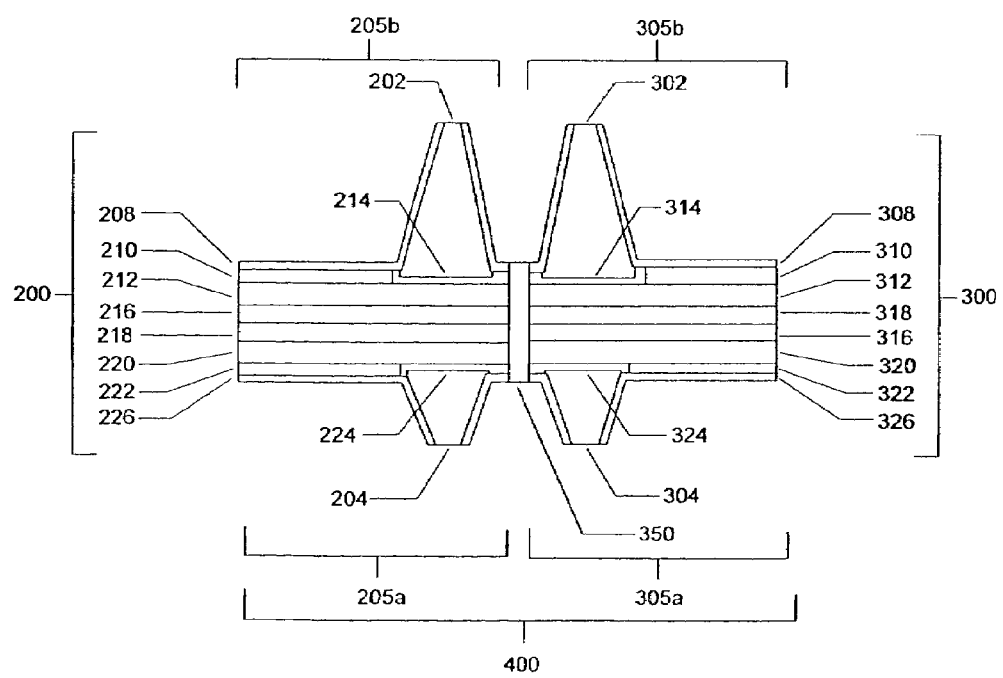
FIG. 18 is a cross-section taken along the plane of line XIV—XIV of FIG. 17.

As illustrated in FIGS. 17–18, the two units, MMRI-IPV (200) and MMRI-IPIR (300), can also exist as a combination unit (MMRI-IPVIR-A) designated at (400), comprised of one MMRI-IPV (200) and one MMRI-IPIR (300). The HPE (202) of the MMRI-IPV (200) and the HPE (302) MMRI-IPIR (300) will be pointed in the same direction on the one side of the MMRI-IPVIR-A. The LPE (204) of the MMRI-IPV (200) and the LPE (304) of the MMRI-IPIR (300) will be also pointed together in the same direction, but on the opposite side of the MMRI-IPVIR-A (400) and in a direction opposite the direction of the HPEs (202, 302).

Figure 21:
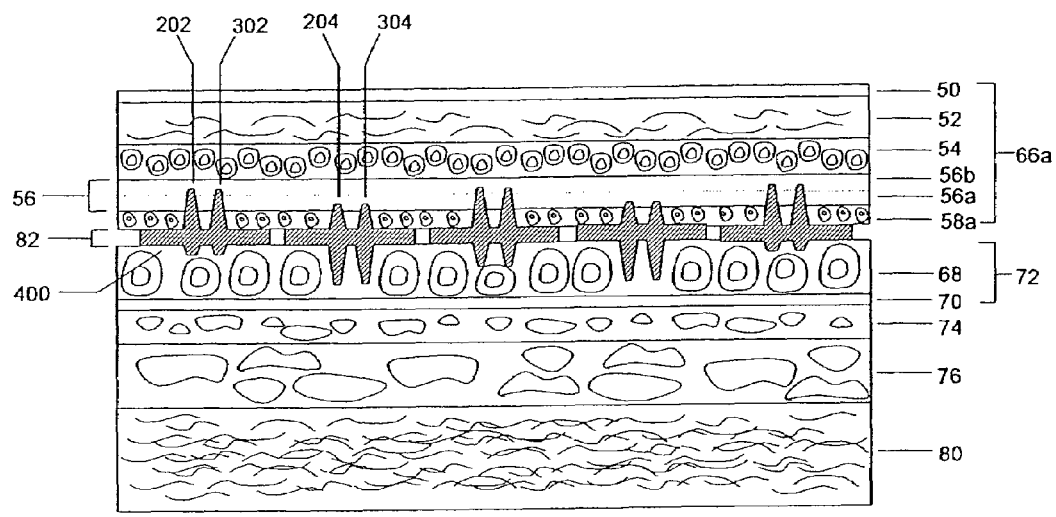
FIG. 21 is a cross-section of the retina showing the microphotodiode implants of FIG. 17 (MMRI-IPVIR-A) in their preferred location in the subretinal space, with their electrodes penetrating into the sublamina B, and sublamina A locations of the inner plexiform.

As illustrated in FIG. 21, the MMRI-IPVIR-A (400) are disposed in the subretinal space (82) of the eye, and are used to stimulate those retinas where the photoreceptor layer has completely degenerated leaving the bipolar cell layer (58a) or the inner plexiform layer (56) as the layer adjacent to the subretinal space (82). Since the "light channel" inner plexiform layer known as sublamina "B" (56b) is further away from the subretinal space (82) compared to the "dark channel" inner plexiform layer known as sublamina "A" (56a), the HPE electrodes (202, 302) will selectively contact the "light channel" synapses in the sublamina "B" (56b) and the LPEs (204, 304) will selectively contact the "dark channel" synapses in sublamina "A" (56A) This arrangement will allow a visible light stimulus to selectively depolarize and activate the light channels in sublamina "B" by causing a negative electric current to be produced by the HPE (202), and an IR light stimulus to selectively hyperpolarize and inhibit the light channels in sublamina "B" by causing a positive electric current to be produced by the HPE (302). This arrangement will also allow an IR light stimulus to selectively depolarize and activate the dark channels in sublamina "A" by causing a negative electric current to be produced by the LPE (304), and a visible light stimulus to selectively hyperpolarize and inhibit the dark channels in sublamina "A" by causing a positive electric current to be produced by the LPE (204).

Figure 22:
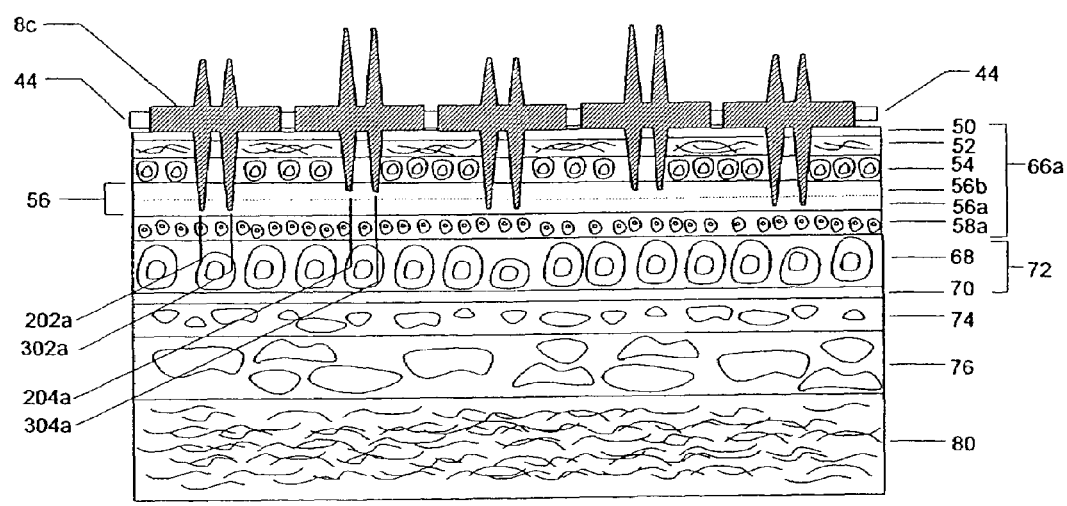
FIG. 22 is a cross-section of the retina showing the microphotodiode implants of FIG. 17 with reversed polarities (MMRI-IPVIR-AR), in a ninth embodiment of this invention, in their preferred location on the nerve fiber layer surface, with their electrodes penetrating into the sublamina B, and sublamina A location of the inner plexiform.

As illustrated in FIGS. 12 and 22, in another embodiment, MMRI-4 (8), and reversed polarity MMRI-IPVIR-A implants called for convenience, MMRI-IPVIR-ARs (8c), are embedded into a biologically compatible sheet (44) that allows the electrode surfaces of the devices to be exposed.

As shown in FIG. 12, the sheet (44), with the embedded MMRI-4 (8) is placed on the internal limiting membrane surface (50) of the retina from the vitreous body side. From this location, MMRI-4s (8) will stimulate the Nerve Fiber Layer (52) and/or Ganglion Cells (54) of the retina.

As shown in FIG. 22, in the case of the MMRI-IPVIR-ARs (8c), their electrodes will penetrate the nerve fiber (52) and ganglion cell layer (54) into the sublamina "B" light channel layer (56b), and sublamina "A" dark channel layer (56a) regions of the inner plexiform layer (56) to selectively stimulate those layers to induce visual sensations. The reverse polarity of the MMRI-IPVIR-ARs (8c) compared to the MMRI-IPVIR-As (400) of FIG. 21 is necessary to preserve the visible light stimulus's effect of depolarizing (activating) the light channels of sublamina "B" (56b) while hyperpolarizing (inhibiting) the dark channels of sublamina "A" (56a); and an IR light stimulus's effect of depolarizing (activating) the dark channels of sublamina "A" (56a) while hyperpolarizing (inhibiting) the light channels of sublamina "B" (56b). It should be noted that polarization changes, i.e. hyperpolarization and depolarization, do not have the same effect in the subretinal space on remanent photoreceptor cells as they do in the sublamina B and A regions of the IPL. In the subretinal space, a hyperpolarizing stimulus produces a sensation of light in the remanent photoreceptor cells while a depolarizing stimulus produces a sensation of darkness in remanent photoreceptor cells.

Figure 13:
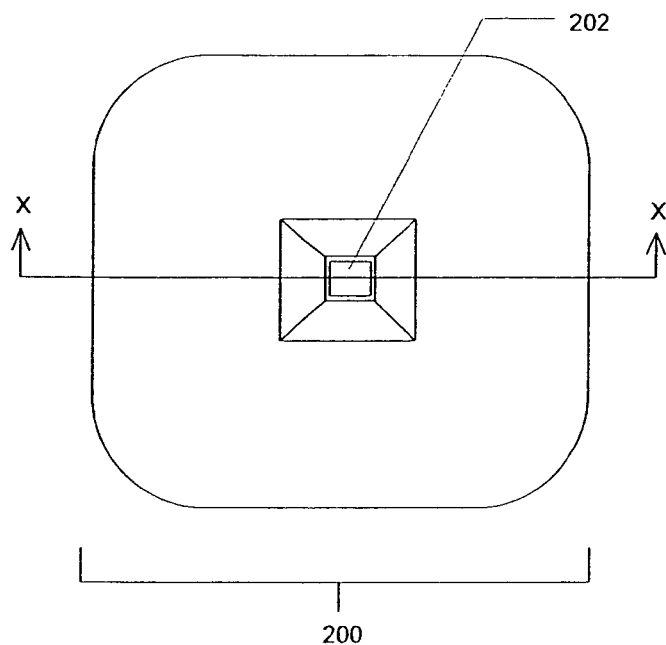
FIG. 13 shows a plan view of a fifth embodiment of the microphotodiode implant of this invention (MMRI-IPV)
Figure 14:
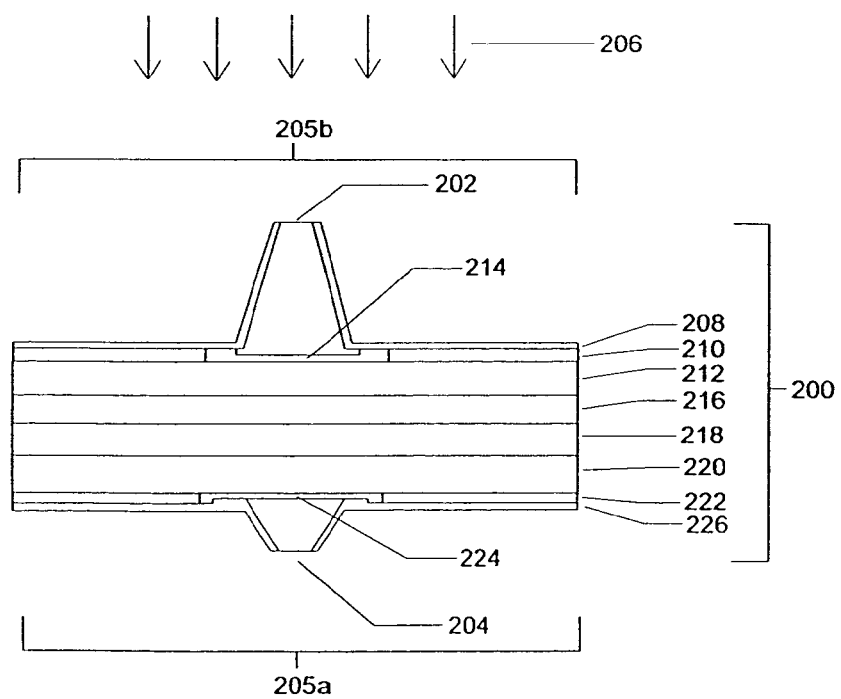
FIG. 14 is a cross-section take along the plane of line X—X of FIG. 13.

FIGS. 13–14 therefore illustrate a fifth embodiment of this invention referred to for convenience as a "MMRI-IPV", and is sized in microscopic dimensions, and is designated at (200). MMRI-IPV (200) is a physically independent unit with its layered microarchitecture shown in FIG. 14. In this embodiment, the MMRI-IPV (200) forms the shape of a flattened cube with rounded corners and edges, with an electrically negative high projecting electrode ("HPE") (202), and an electrically positive low projecting electrode (LPE") (204). A MMRI-IPV (200) may function as a PiN or NiP device when stimulating the inner retina, depending upon which of its two photosensitive sides, the P side (205a) or the N side (205b) is stimulated by visible light (206). From top to bottom, the layers of the MMRI-IPV (200) are as follows: A negative HPE electrode (202) preferably made of gold, an insulating layer of $SiO_2$ (208) which covers the N side (205b) except for the tip of the HPE electrode (202), a multilayer dielectric filter (210) to allow passage of only visible light (400 nm to 740 nm), a N+ layer (212), a contact pad (214) fabricated from any of the following, and/or any compounds of the following: gold, aluminum, titanium, and chromium, to establish electrical contact between the negative HPE (202) and the N+ layer (212), a N-type silicon substrate layer (216), an intrinsic layer (218) which forms naturally between the N-type silicon substrate layer (216), and the next P+ layer (220), a multilayer dielectric filter (222) to allow passage of only visible light (400 nm to 740 nm), a contact pad (224) fabricated from any of the following, and/or any compounds of the following: gold, aluminum, titanium, and chromium to establish electrical contact between the P+ layer (220) and the electrically positive low projecting electrode (LPE) (204). An insulating layer of $SiO_2$ (226) covers the P side (205a) except for the tip of the LPE electrode (204).

Figure 15:
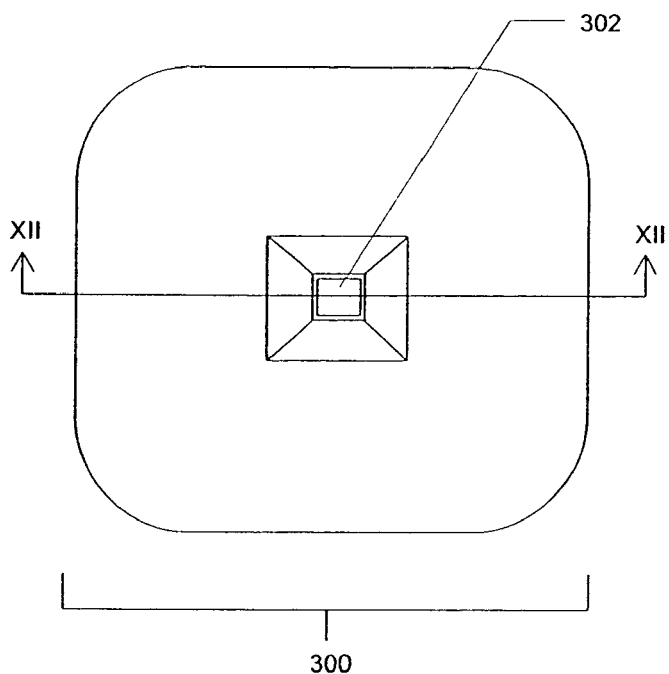
FIG. 15 shows a plan view of a sixth embodiment of the microphotodiode implant of this invention (MMRI-IPIR)
Figure 16:
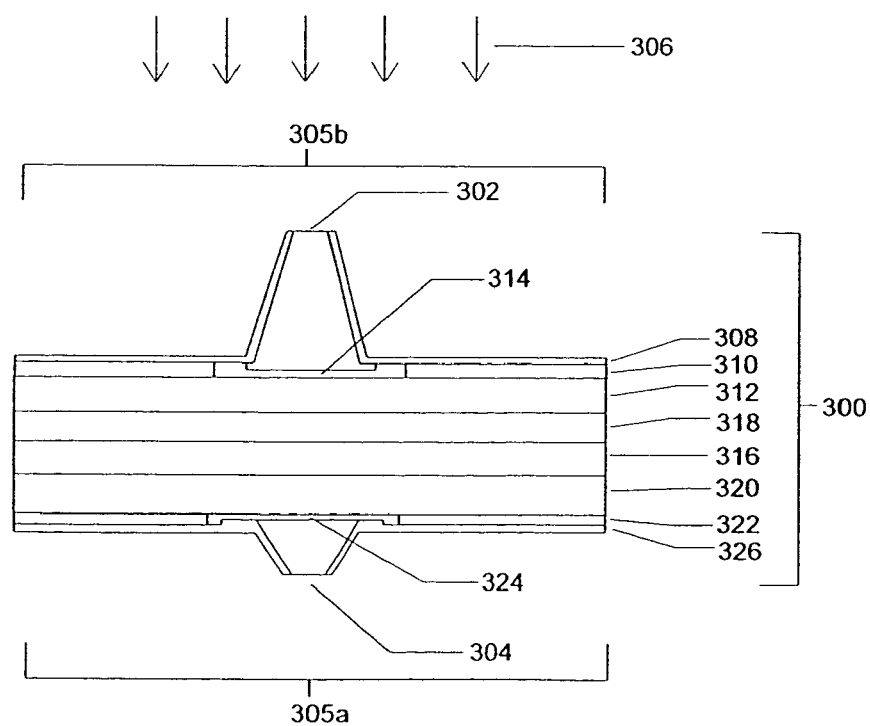
FIG. 16 is a cross-section taken along the plane of line XII—XII of FIG. 15.

FIGS. 15–16 illustrates a sixth embodiment of this invention referred to for convenience as a "MMRI-IPIR", and is sized in microscopic dimensions, and is designated at (300). As illustrated, a MMRI-IPIR (300) is a physically independent unit with its layered microarchitecture is shown in FIG. 16. In this embodiment, the MMRI-IPIR (300) forms the shape of a flattened cube with rounded corners and edges, with an electrically positive high projecting electrode (HPE) (302), and an electrically negative low projecting electrode (LPE) (304). The MMRI-IPIR (300) is sized in microscopic dimensions. A MMRI-IPIR (300) may function as a PiN or NiP device when stimulating the inner retina, depending upon which of its two photosensitive sides, the N-side (305a) or the P-side (305b) is stimulated by infrared light (306). From top to bottom, the layers of the MMRI-IPIR (300) are as follows: A positive HPE electrode (302) preferably made of gold, an insulating layer of $SiO_2$ (308) which covers the P side (305b) except for the tip of the positive HPE electrode (302), a multilayer dielectric filter (310) to allow passage of only IR light (740 nm to 900 nm), a P+ layer (312), a contact pad (314) fabricated from any of the following and/or any compounds of the following: gold, aluminum, titanium, and chromium, to establish electrical contact between the positive HPE (302) and the P+ layer (312), an intrinsic layer (318) which forms naturally between the P+ layer (312) and the next N-type silicon substrate layer (316), a N+ layer (320), a multilayer dielectric filter (322) to allow passage of only IR light (740 nm to 900 nm), a contact pad (324) fabricated from any of the following and/or any compounds of the following: gold, aluminum, titanium, and chromium to establish electrical contact between the N+ layer (320) and the electrically negative low projecting electrode (LPE) (304). An insulating layer of SiO2 (326) covers the N side (305a) except for the tip of the LPE electrode (304).

FIGS. 17–18 illustrate a seventh embodiment of this invention referred to for convenience as a "MMRI-IPVIR A", and is sized in microscopic dimensions, and is designated at 400. It is composed of one MMRI-IPV (200), and one MMRI-IPIR (300), separate by a layer of channel block (350). The layered microarchitecture of the MMRI-IPV component (200) is shown on the left side and is described first. The MMRI-IPV component (200) forms the shape of one-half of a flattened cube with rounded external corners and edges, with an electrically negative high projecting electrode (HPE) (202), and an electrically positive low projecting electrode (LPE) (204). From top to bottom, the layers of the MMRI-IPV (200) are as follows: A negative HPE electrode (202) preferably made of gold, an insulating layer of SiO2 (208) which covers the N side (205b) except for the tip of the HPE electrode (202), a multilayer dielectric filter (210) to allow passage of only visible light (400 nm to 740 nm), a N+ layer (212), a contact pad (214) fabricated from any of the following and/or any compounds of the following: gold, aluminum, titanium, and chromium, to establish electrical contact between the negative HPE (202) and the N+ layer (212), a N-type silicon substrate layer (216), an intrinsic layer (218) which forms naturally between the N-type silicon substrate layer (216), and the next P+ layer (220), a multilayer dielectric filter (222) to allow passage of only visible light (400 nm to 740 nm), a contact pad (224) fabricated from any of the following and/or any compounds of the following: gold, aluminum, titanium, and chromium to establish electrical contact between the P+ layer (220) and the electrically positive low projecting electrode (LPE) (204). An insulating layer of SiO2 (226) covers the P side (205a) except for the tip of the LPE electrode (204). The layered microarchitecture of the MMRI-IPIR component (300) of the MMRI-IPVIR-A (400) is shown on the right side and is now described. The MMRI-IPIR component (300) forms the shape of one-half of a flattened cube with rounded external corners and edges, with an electrically positive high projecting electrode (HPE) (302), and an electrically negative low projecting electrode (LPE) (304). From top to bottom, the layers of the MMRI-IPIR (300) are as follows: A positive HPE electrode (302) preferably made of gold, an insulating layer of SiO2 (308) which covers the P side (305b) except for the tip of the positive HPE electrode (302), a multilayer dielectric filter (310) to allow passage of only IR light (740 nm to 900 nm), a P+ layer (312), a contact pad (314) fabricated from any of the following and/or any compounds of the following: gold, aluminum, titanium, and chromium, to establish electrical contact between the positive HPE (302) and the P+ layer (312), an intrinsic layer (318) which forms naturally between the P+ layer (312) and the next N-type silicon substrate layer (316), a N+ layer (320), a multilayer dielectric filter (322) to allow passage of only IR light (740 nm to 900 nm), a contact pad (324) fabricated from any of the following and/or any compounds of the following: gold, aluminum, titanium, and chromium to establish electrical contact between the N+ layer (320) and the electrically negative low projecting electrode (LPE) (304). An insulating layer of SiO2 (326) covers the N side (305a) except for the tip of the LPE electrode (304).

Figure 19:
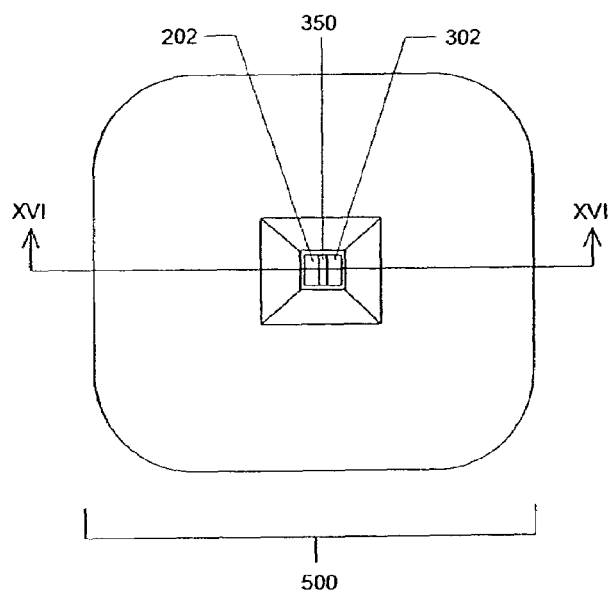
FIG. 19 shows a plan view of a eighth embodiment of the microphotodiode implant of this invention (MMRI-IPVIR-B)
Figure 20:
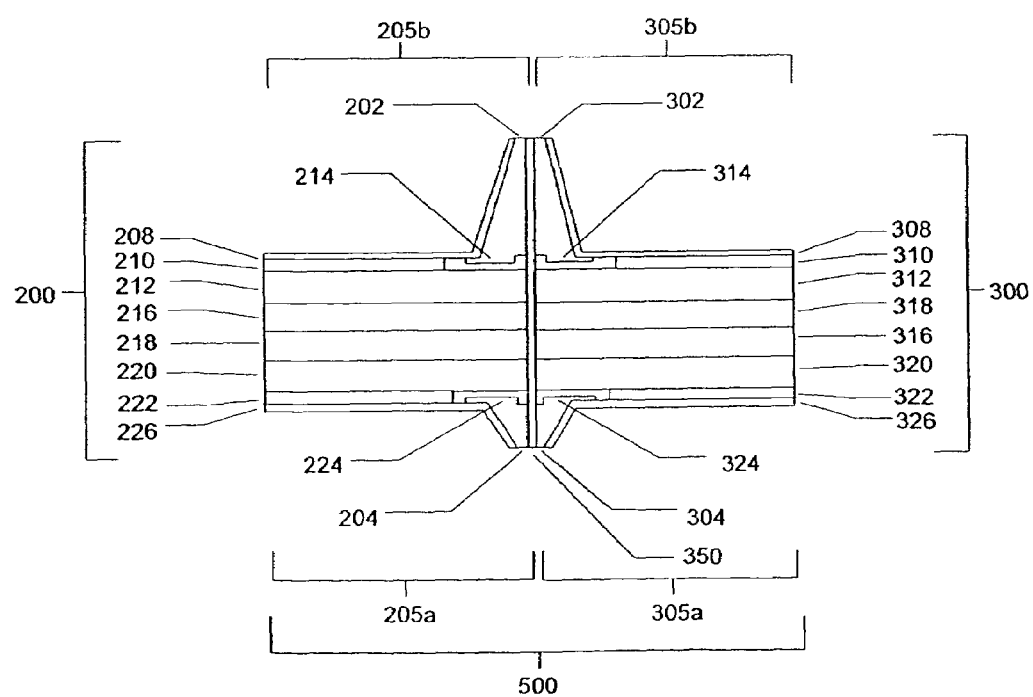
FIG. 20 is a cross-section taken along the plane of line XVI—XVI of FIG. 19.

FIGS. 19–20 illustrate an eighth embodiment of this invention referred to for convenience as a "MMRI-IPVIR-B", and is sized in microscopic dimensions, and is designated at 500. It is composed of one MMRI-IPV (200), and one MMRI-IPIR(300), separate by a layer of channel block (350). The layered microarchitecture of the MMRI-IPV component (200) is shown on the left side and is described first. The MMRI-IPV component (200) forms the shape of one-half of a flattened cube with rounded external corners and edges, with an electrically negative high, projecting electrode (HPE) (202), and an electrically positive low projecting electrode (LPE) (204). From top to bottom, the layers of the MMRI-IPV (200) are as follows: A negative HPE electrode (202) preferably made of gold, an insulating layer of $SiO_2$ (208) which covers the N side (205b) except for the tip of the negative HPE electrode (202), a multilayer dielectric filter (210) to allow passage of only visible light (400 nm to 740 nm), a N+ layer (212), a contact pad (214) fabricated from any of the following and/or any compounds of the following: gold, aluminum, titanium, and chromium, to establish electrical contact between the negative HPE (202) and the N+ layer (212), a N-type silicon substrate layer (216), an intrinsic layer (218) which forms naturally between the N-type silicon substrate layer (216), and the next P+ layer (220), a multilayer dielectric filter (222) to allow passage of only visible light (400 nm to 740 nm), a contact pad (224) fabricated from any of the following and/or any compounds of the following: gold, aluminum, titanium, and chromium to establish electrical contact between the P+ layer (220) and the electrically positive low projecting electrode (LPE) (204). An insulating layer of $SiO_2$ (226) covers the P side (205a) except for the tip of the LPE electrode (204). The layered microarchitecture of the MMRI-IPIR component (300) of the MMRI-IPVIR-B (500) is shown on the right side and is now described. The MMRI-IPIR component (300) forms the shape of one-half of a flattened cube with rounded external corners and edges, with an electrically positive high projecting electrode (HPE) (302), and an electrically negative low projecting electrode (LPE) (304). From top to bottom, the layers of the MMRI-IPIR (300) are as follows: A positive HPE electrode (302) preferably made of gold, an insulating layer of $SiO_2$ (308) which covers the P side (305b) except for the tip of the positive HPE electrode (302), a multilayer dielectric filter (310) to allow passage of only IR light (740 nm to 900 nm), a P+ layer (312), a contact pad (314) fabricated from any of the following and/or any compounds of the following: gold, aluminum, titanium, and chromium, to establish electrical contact between the positive HPE (302) and the P+ layer (312), an intrinsic layer (318) which forms naturally between the P+ layer (312) and the next N-type silicon substrate layer (316), a N+ layer (320), a multilayer dielectric filter (322) to allow passage of only IR light (740 nm to 900 nm), a contact pad (324) fabricated from any of the following and/or any compounds of the following: gold, aluminum, titanium, and chromium to establish electrical contact between the N+ layer (320) and the electrically negative low projecting electrode (LPE) (304). An insulating layer of $SiO_2$ (326) covers the N side (305a) except for the tip of the LPE electrode (304).

FIG. 21 shows MMRI-IPVIR-As (400) implanted in their preferred monolayer position in the subretinal space (82). The depolarizing high projecting electrodes (HPEs) (202) from the visible light sensing portion of the microphotodiodes stimulate the light channels in sublamina B (56b) of the inner plexiform layer (IPL) (56). The hyperpolarizing HPEs (302) from the IR light sensing portion of the microphotodiodes (for darkness detection) inhibit the light channels in sublamina B (56b) of the IPL (56). The depolarizing low projecting electrodes (LPEs) (304) from the IR light sensing portion of the microphotodiodes (for darkness detection) stimulate the dark channels in sublamina A (56a) of the IPL (56). The hyperpolarizing LPEs (204) from the visible light sensing portion of the microphotodiode inhibit the dark channels in sublamina A (56a) of the IPL (56). The layers of the eye, in this schematic of a partially degenerated retina, at the posterior pole from inside the eye to outside the eye are: internal limiting membrane (50); nerve fiber layer (52); ganglion cell layer (54); inner plexiform layer (56) consisting of sublamina b (56b) and sublamina a (56a); and the partially degenerated inner nuclear layer (58a). The MMRI-IPVIR-A (400) are disposed between the partially degenerated inner retinal layer (66a), and the retinal pigment epithelium (68) and Bruch's membrane (70), which together constitute the outer retinal layer (72). External to the outer retinal layer (72) are the choriocapillaris (74), choroid (76), and sclera (80). Alternatively, instead of MMRI-IPVIR-As (400), component MMRI-IPVs and MMRI-IPIRs of FIGS. 13–16, or MMRI-IPVIR-Bs of FIGS. 19–20 can be implanted into the subretinal space (82).

FIG. 22 shows MMRI-IPVIR-ARs (8c) in a ninth embodiment of this invention, positioned on the internal limiting membrane surface (50) of the retina. In this embodiment, MMRI-IPVIR-ARs (8c) are embedded into a flexible, biologically compatible sheet (44), which allows both of the photoactive surfaces and their projecting electrodes of each MMRI-IPVIR-ARs (8c) to be exposed. The depolarizing high projecting electrodes (HPEs) (302a) on the opposite side of the IR sensing microphotodiodes (for darkness detection) penetrate into the dark channels in sublamina A (56a) of the inner plexiform layer (IPL) (56) to stimulate the sensation of darkness. The hyperpolarizing HPEs (202a) on the opposite side of the visible light sensing portion of the microphotodiodes penetrate into the sublamina A (56a) of the IPL (56) to inhibit the dark channels. The depolarizing low projecting electrodes (LPEs) (204a) on the opposite side of the visible light sensing portion of the microphotodiodes penetrate into sublamina B (56b) of the IPL (56) to stimulate the light channels. The hyperpolarizing LPEs (304a) on the opposite side of the IR light sensing portion of the microphotodiode (for sensing darkness) penetrate into sublamina B (56b) of the IPL (56) to inhibit the light channels. The layers of the eye at the posterior pole from inside the eye to outside the eye in this schematic of a partially degenerated retina are: internal limiting membrane (50); nerve fiber layer (52); ganglion cell layer (54); inner plexiform layer (56) consisting of sublamina b (56b) and sublamina a (56a); the partially degenerated inner nuclear layer (58a); all of which constitute the partially degenerated inner retinal layer (66a). The retinal pigment epithelium (68) and Bruch's membrane (70), together constitute the outer retinal layer (72). External to the outer retinal layer (72) are the choriocapillaris (74), choroid (76), and sclera (80). In a subset embodiment, MMRI-IPVIR-ARs (8c) may be fabricated as component opposite polarity MMRI-IPVs and component opposite polarity MMRI-IPIRs, embedded into a flexible, biologically compatible sheet (44), which allows both of the photoactive surfaces and their projecting electrodes of each opposite polarity MMRI-IPV and opposite polarity MMRI-IPIR to be exposed.

Figure 23:
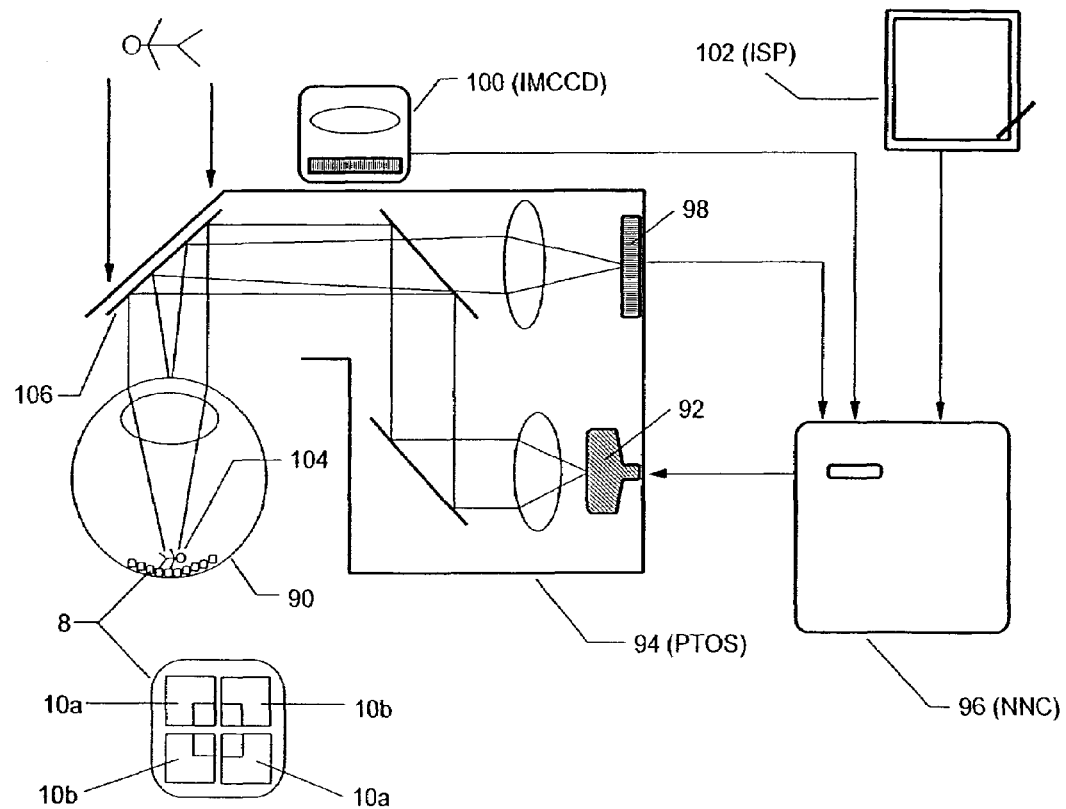
FIG. 23 is a generalized schematic diagram of the Adaptive Imaging Retinal Stimulation System (AIRES) showing its component sub-systems of: the Projection and Tracking Optical System (PTOS), the Neuro-Net Computer (NNC), and the Input Stylus Pad (ISP). Q-SEMCPs are shown implanted in the eye.

FIG. 23 is a schematic diagram of the Adaptive Imaging Retinal Stimulation System (AIRES) showing its component subsystems of: the Projection and Tracking Optical System (PTOS) headset (94), the Neuro-Net Computer (NNC) (96), the Imaging CCD Camera (IMCCD) (100) and the Input Stylus Pad (ISP) (102). A Pupil Reflex Tracking CCD (PRTCCD) (98), and an IR/visible CRT display (IRVCRT) (92) is inside the PTOS (94). MMRI-4s (8) are shown in the subretinal space of the eye (90). During function, IR and visible light images from the IRVCRT (92) within the PTOS (94) are optically projected onto the eye (90). Intensity, wavelength duration, and pulsing of the images is controlled by the NNC (96) and modulated by patient inputs via the interfaced ISP (102). The IMCCD (100), which is mounted on or in the PTOS headset (94), provides the image inputs to the NNC (96) which in turn programs the visible and IR image outputs of the IRVCRT (92). A PRTCCD (98) is integrated into the PTOS headset (94) to track eye movements via changes in the position of the pupillary Purkinje reflexes. The PRTCCD (98) will output to the NNC (96) which in turn will direct the aim of the IMCCD (100) via servo motor control to follow the eye movements. The PTOS (94) also may be programmed to provide just a diffuse IR illumination to interact with ambient visible light images (104) on the MMRI-4s (8).

The detailed operation of the AIRES system is as follows. A patient with a large plurality of implanted MMRI-4s (8) will see pixelated images, cause by localized subretinal hyperpolarization, produced by the PiN configuration of the MMRI-4 subunits (10a). These electrically induced images are caused by the light from incoming ambient images (104) which pass through an external partially reflective and transmissive mirror (106) of the PTOS (94). Images of dark details are induced by depolarizing currents produced by the NiP configuration of MMRI-4 subunits (10b), which are stimulated by IR illumination and/or images provided by the IRVCRT (92). The IRVCRT (92) is programmed by the NNC (96) to provide diffuse IR illumination and/or IR images to superimpose upon the visible light images (104) from incoming light. Image information for the NNC (96) is obtained from the interfaced IMCCD (100). Diffuse IR illumination from the IRVCRT (92) will induce a constant depolarizing "bias current" from the MMRI-4 NiP subunits (10b). This "bias current" will produce the sensation of darkness in the absence of light stimulation to the PiN subunits (10a). However, when light is present to stimulate the PiN subunits (1a), the resultant hyperpolarizing current will offset the IR induced NiP depolarizing bias current. The result is the perception by the patient of a sensation of light. Because of the limited bandwidth sensitivity of the IR NiP configuration (10b) (740 nm–900 nm), environmental IR "noise" is minimal. The amount of NiP depolarizing bias current will be initially adjusted by the patient via the ISP (102) and this information will be input into the NNC (96). It is then correlated with image processed information coming from the interfaced IMCCD (100). The appropriate amount of NiP "bias current", base upon environmental lighting conditions and images, will then be "learned" by the NNC (96). With additional learning, the NNC (96) will be able to anticipate the amount of NiP "bias current" needed to produce more accurate patient perceived images, without the need for patient input.

The entire visible light image may also be projected by the IRVCRT (92) simultaneously, or in rapid alternation with IR image pulses to entirely control MMRI-4(B) function. In this situation, the partially reflective/transmissive mirror (106) of the PTOS (94), is replaced with a completely reflective mirror, to prevent ambient light images (104) from stimulating the MMRI-4s (8). By programming the pulse duration and frequency of IR and visible-light images, color vision may possibly be induced, similar to the effect of the Benham top. This phenomenon has also been used in black and white television displays to create the perception of color images in normal sighted persons.

Figure 24:
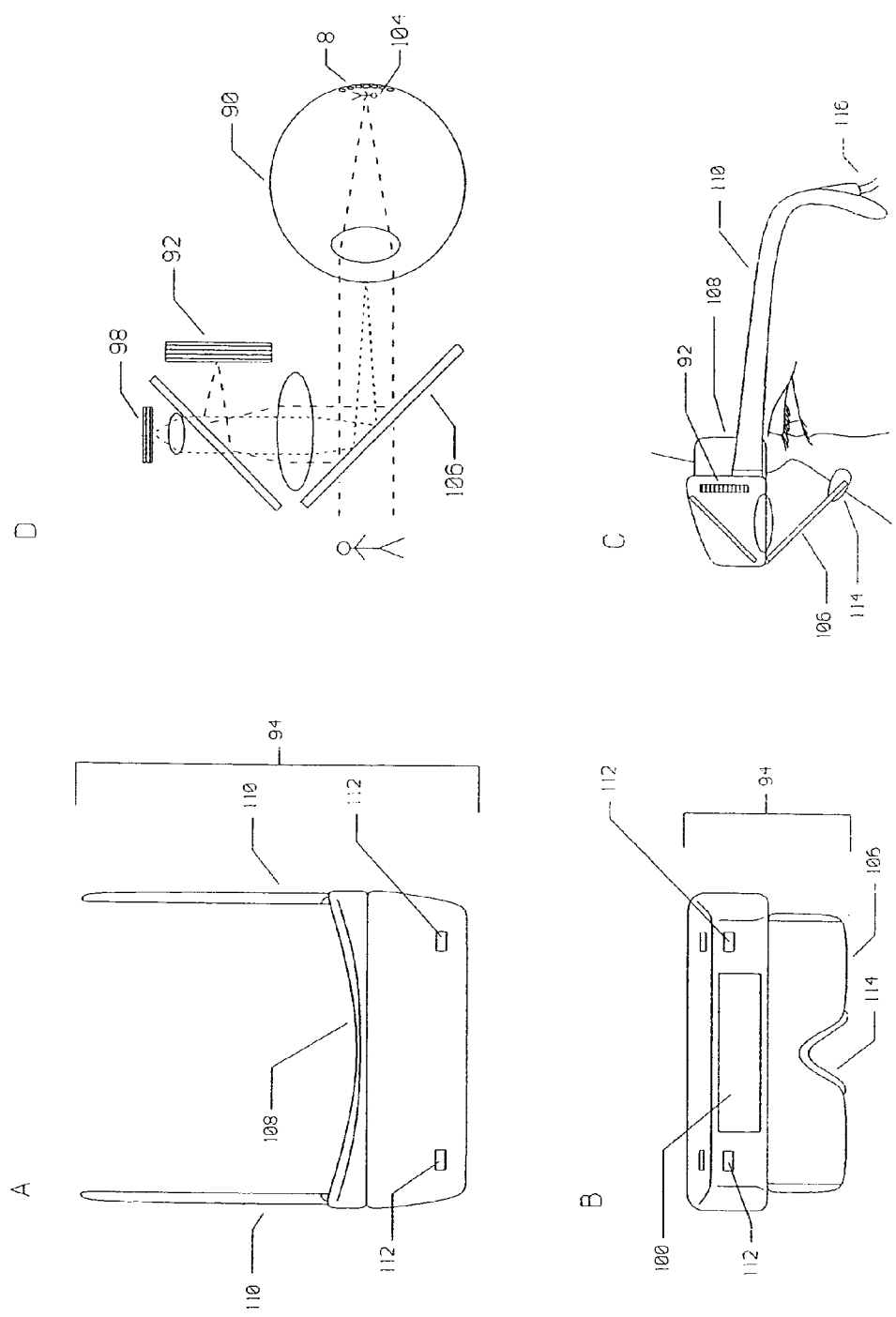
FIGS. 24A–D shows a PTOS device configured as a glasses headset, and the schematic of its optics.

FIG. 24, A through D shows a glasses-like configuration (94) of the PTOS component of the AIRES system. As seen in FIG. 24D, although the schematic of the optical system differs somewhat from the generalize schematic of the PTOS component (94) demonstrated in FIG. 23, the spirit and function of both versions of the devices are the same. FIG. 24A is a top view of the PTOS (94). It shows the head-pad (108), the temple pieces (110), and the ambient light intensity sensors (112). FIG. 24B is a front view of the PTOS (94). It shows the external partially reflective/transmissive mirror (106), a supporting nose piece (114), ambient light intensity sensors (112), and the window for the IMCCD (100) shown in the FIG. 23 schematic. FIG. 24C is a phantom side view of the PTOS (94). It shows an internal infrared and visible light capable LED light source (92), which has been substituted for the IRVCRT (92) of FIG. 23. Also shown is the partially reflective/transmissive mirror (106), the supporting nose piece (114), the head-pad (108), one of the temple pieces (110), and the power supply and signal wire cable (116) to the NNC (96) of FIG. 23. FIG. 24D is a schematic of the PTOS (94). It shows the MMRI-4s (8) disposed in the subretinal space of the eye (90) with an ambient focused image (104). It also shows the internal infrared and visible light capable LED light source (92), the PRTCCD (98), and the external partially reflective/transmissive mirror (106).

Figure 25:
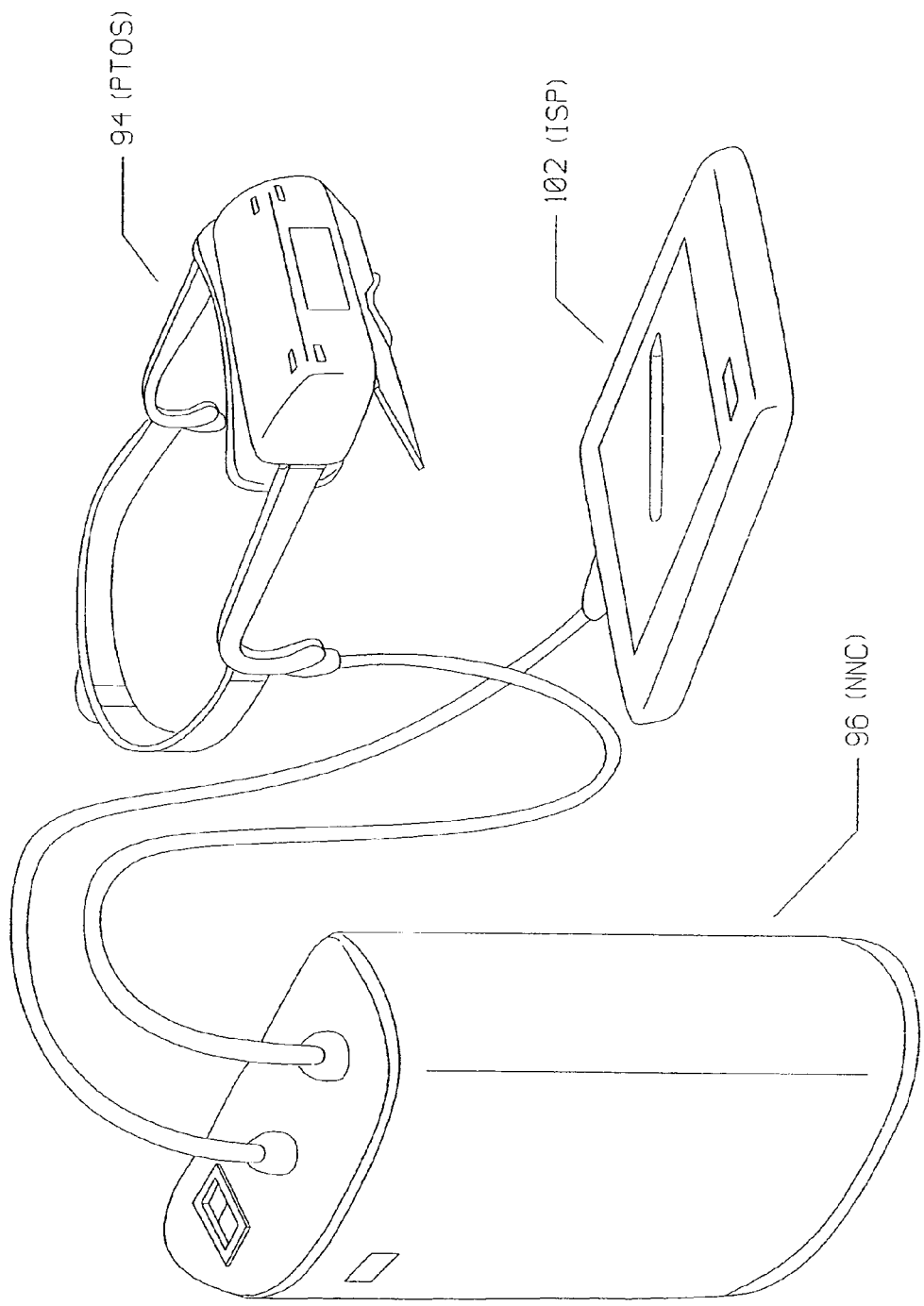
FIG. 25 shows the components of the AIRES system, consisting of the PTOS, the NNC, and ISP.

FIG. 25 is diagram showing the components of the AIRES system, consisting of the PTOS (94), the portable NNC (96) which may be secured to the patient's body, and the ISP (102) input device.

Figure 26:
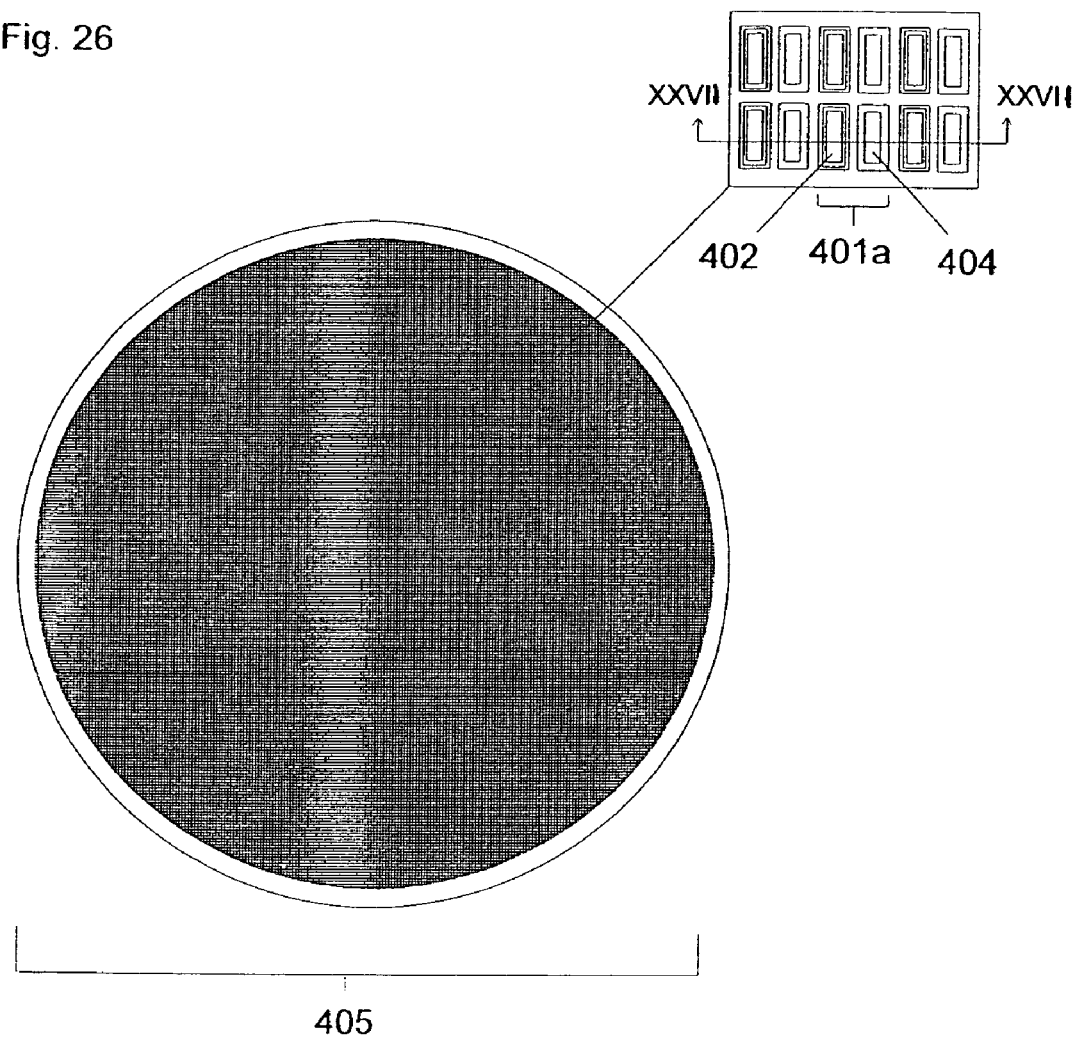
FIG. 26 is a plan view (containing a detail exploded inset view) of a large wafer containing a ninth embodiment of an implant of this invention ("MMRI-OPSISTER-D").

FIG. 26 is a plan view (containing a detail exploded inset view) of a large wafer containing a ninth embodiment of an implant of this invention. This ninth embodiment is based on a microphotodiode (401a) (referred to hereinafter as an "MMRI-OPSISTER-D"). Each MMRI-OPSISTER-D microphotodiode (401a) has two microphotodiode subunits (402) and (404), as shown in the exploded inset view in FIG. 26.

As will be discussed below, the large wafer (405) can be cut into smaller wafer-type implants (e.g. wafers of about 0.25 to 15 mn (e.g. thousands to tens of thousands) of MMRI OPSISTER-D microphodiode units (401a). Alternately, large wafer (405) can be diced into even smaller discrete-type implants (e.g. implants of between 1 micron and 0.25 mm containing one to 10,000 MMRI OPSISTER-D microphodiode units (401a). Whether a wafer-type implant or discrete implants are made, many of the fabrication steps and the basic structure of the MMRI OPSISTER-D microphodiode (401a) is the same.

FIGS. 27A–E illustrate, in perspective cross-sectional views taken at section XXVII—XXVII of the MMRI-OPSISTER-D (401a) of FIG. 26, the fabrication steps and structure of the MMRI-OPSISTER-D (401a). In the initial fabrication step (FIG. 27A) microphotodiode subunits (402) and (404) of the MMRI-OPSISTER (401) are formed using photomask, ion implantation and heat drive-in techniques applied to both sides of a starting N bulk thinned wafer (405) of FIG. 26). From top to bottom in FIG. 27A, the microphotodiode subunit (402) has a P+ layer (406), an intrinsic layer (408), an N bulk layer (409) and a N+ layer 410. The microphotodiode subunit (404) has a N+ layer (410a), an N bulk layer (409a), an intrinsic layer (408a) and a P+ layer (406a). Separating electrically the two microphotodiode subunits (402 and 404) from one another and from other MMRI-OPSISTERs on the same substrate is P+ channel block (412) surrounding the subunits (402 and 404).

Figure 27A:
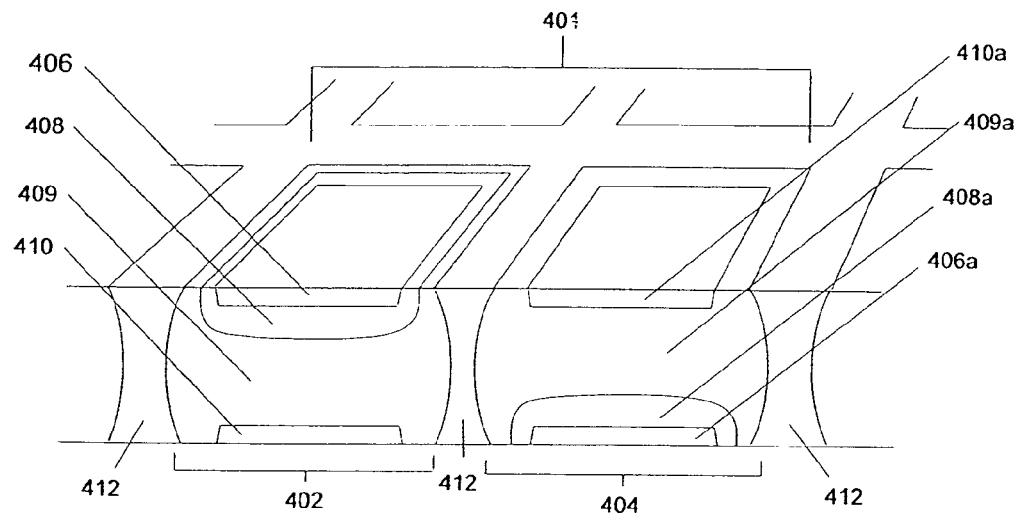
FIGS. 27A–E are perspective views in cross-section taken along the plane of line XXVI—XXVI of FIG. 26 showing the fabrication steps an the MMRI-OPSISTER-D of FIG. 26.
Figure 27B:
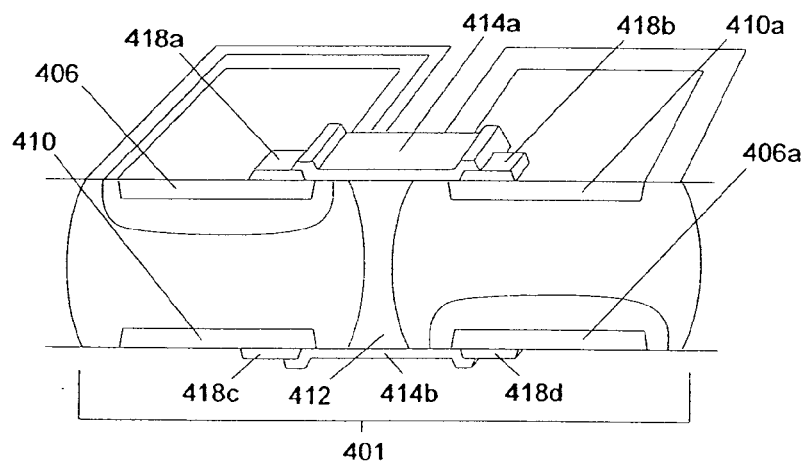

FIG. 27B shows aluminum contact pads (418a–d) that are deposited and heat driven-in into the P+ and N+ surfaces (406, 406a, 410, and 410a). Bridging the contact pads (418a–d) between the P+ and N+ surfaces (406, 406a, 410, and 410a) of each side of the MMRI-OPSISTER (401) is a silicon dioxide insulator strip (414a and 414b).

Figure 27C:
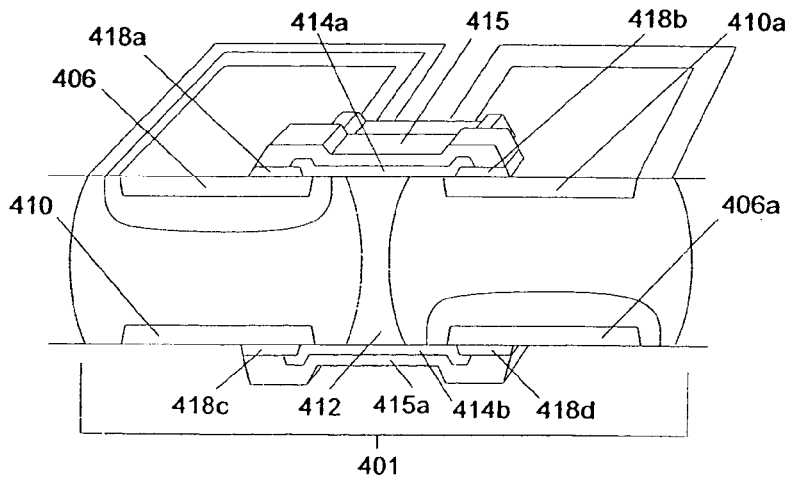

FIG. 27C shows the deposition of aluminum conductors (415 and 415a) over the silicon dioxide insulator strips (414a and 414b) so that the conductor (415) contact the aluminum contact pads (418a and 418b), and conductor (415a) contact the aluminum contact pads (418c and 418d).

Figure 27D:
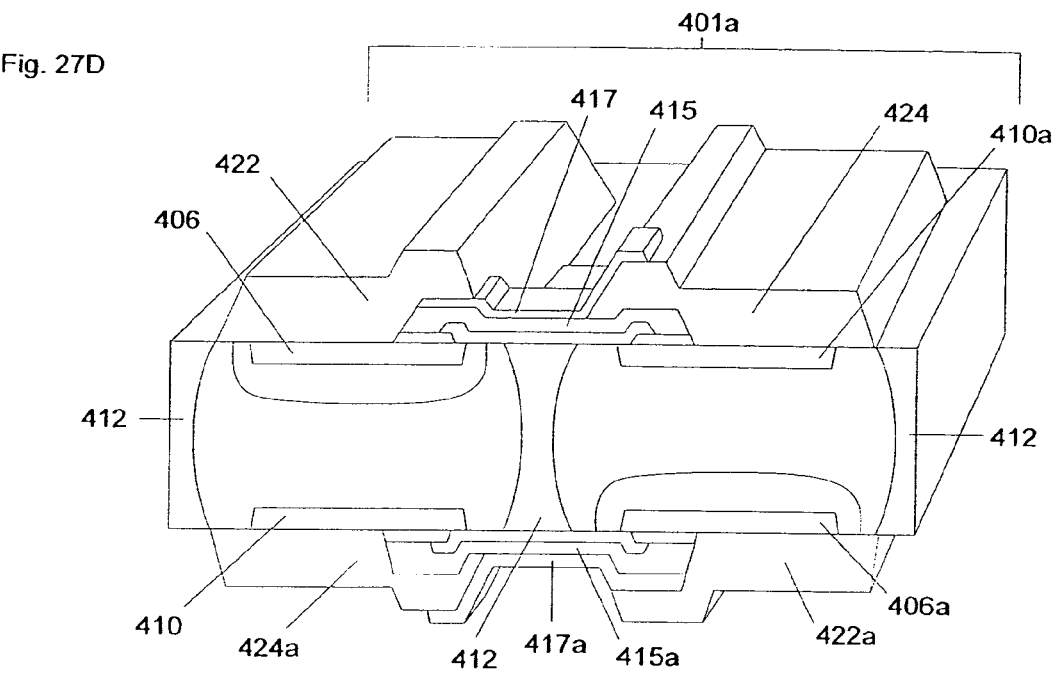

FIG. 27D shows the deposition of infrared-pass dielectric filters (422 and 422a) on the P+ surfaces (406 and 406a), and visible-light-pass dielectric filters (424 and 424a) on the N+ surfaces (410 and 410a). A layer of barrier aluminum (417) needed during the fabrication of dielectric filters (422 and 424) is also deposited on the conductor (415). Similarly another layer of barrier aluminum (417a) needed during the fabrication of dielectric filters (424a and 422a) is deposited on the conductor (415a).

Figure 27E:
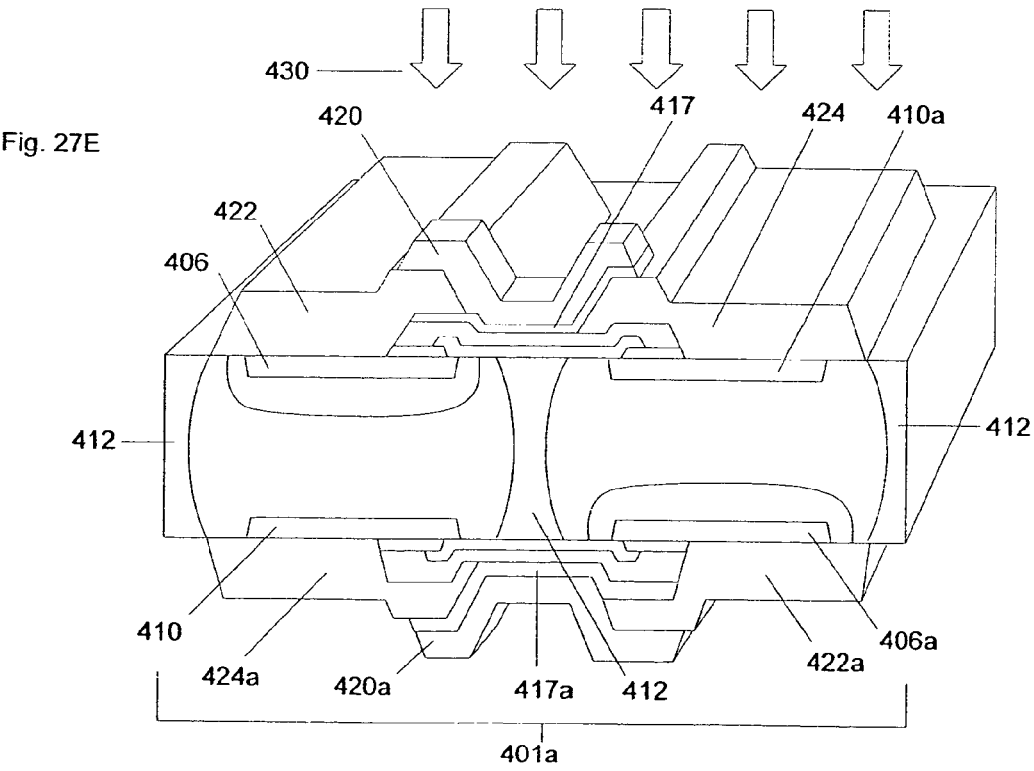

FIG. 27E shows the deposition of the final bridging electrode (420) on the barrier aluminum (417), and the deposition of the final bridging electrode (420a) on the barrier aluminum (417a). The final bridging electrodes (420 and 420a) are fabricated from any biocompatible electrode material or combinations of biocompatible electrode materials such as iridium, platinum, gold, aluminum, ruthenium, rhodium, palladium, tantalum, titanium, chromium, molybdenum, cobalt, nickel, iron, copper, silver, zirconium, tungsten, polysilicon, or compounds, such as oxides, composed of the same. Iridium oxide is the preferred material for the electrodes (420 and 420a). The MMRI-OPSISTER device (401) of FIGS. 27A–C with dielectric light filters is called an MMRI-OPSISTER-D device (401a) in FIGS. 27D,E.

As shown in FIG. 27E, the dielectric light filter layers (422, 422a, and 424, 424a) allow only specific, but different, light bandwidths to pass. In the embodiment illustrated in FIG. 27E, the dielectric filter layers (422 and 422a) that overlay the P+ layers (406 and 406a) allow only IR light to pass, whereas the dielectric layers (424 and 424a) that overlay the N+ layers (410 and 410a) allow only visible light to pass. In other embodiments, the two types of layers can be reversed where the visible light filters are deposited on the P+ layers, and the IR light filters are deposited on the N+ layers. In still other embodiments, filters (422, 422a), and filters (424, and 424a) can allow different portions of visible or infrared light to pass (e.g. filters 422 and 422*a* allow only green light to pass and filters 424, 424*a* allow only red light to pass).

The MMRI-OPSISTER-D device (401*a*) functions to stimulate vision from the subretinal space (82) (see FIG. 11). As discussed above, implants (401*a*) may be diced into discrete physically separate devices as shown in FIG. 27E. In this circumstance, MMRI-OPSISTER-D devices (401*a*) are placed into the subretinal space (designated as 82 in FIG. 11) by injection using a liquid vehicle or embedded in a dissolvable sheet (both previously described).

Figure 28:
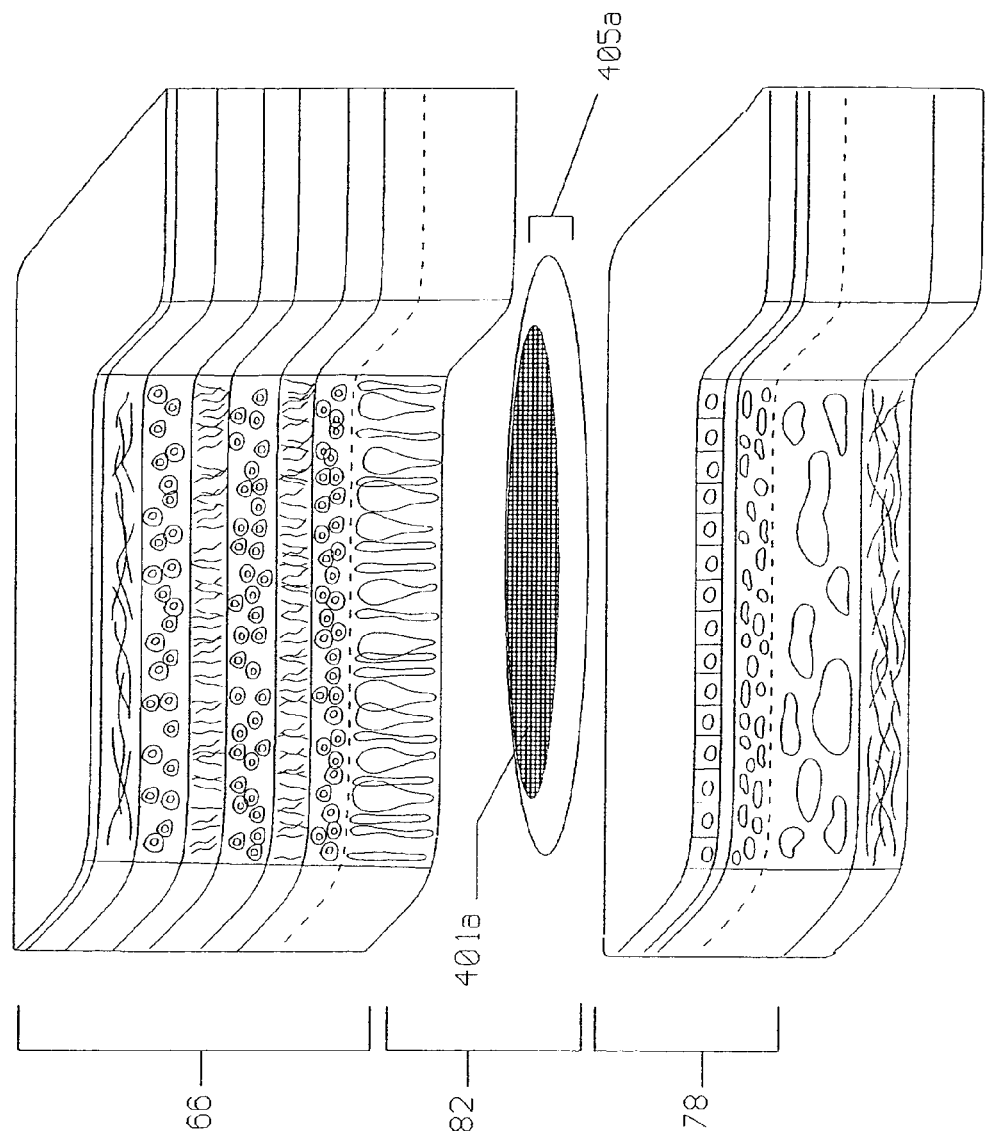
FIG. 28 shows MMRI-OPSISTER-D devices used in a small chip with a beveled edge and implanted into the subretinal space.

As discussed above, large wafer (405) of FIG. 26 can be cut into smaller wafer-type implants (405*a*) (see FIG. 28) of a width (or diameter) ranging from 0.25 mm to 15 mm, preferably from 0.25 mm to 2 mm. Preferably, the edges of implant (405*a*) are rounded or beveled as shown in FIG. 28 to reduce the possibility of the overlaying nerve fiber layer nerve transmission being reduced by a sharp bend in that layer near the edge of the implant.

One or more of the wafer-type implants (405*a*) can then be implanted into the subretinal space (82) between the inner retina (66) and the outer retina (78).

To understand the operation of each MMRI-OPSISTER-D unit (401*a*) (e.g. the one shown in FIG. 27), one should consider the function of a normal, undamaged photoreceptor cell in an eye, and how light and dark images are sensed. In the normal retina, light causes the photoreceptor cell to become more negatively charged internally, whereas the lack of light or a dark image will cause the photoreceptor cell to become less negatively charged internally. The greater internal negativity will cause a signal to be transmitted by the photoreceptor cell to one type of associated bipolar cell which signals that light is sensed. The lesser internal negativity will cause a signal to be transmitted by the photoreceptor cell to another type of associated bipolar cell that signals that darkness (or a dark image) is sensed. These different types of bipolar cells are associated with their respective amacrine and ganglion cells that convert the analog signals of light and darkness produced by the bipolar cells into digital signals that are then sent to the brain and processed as visual information.

As discussed above, therefore, functionally one predominant bandwidth of light shining on the MMRI-OPSISTER-D (401*a*) (e.g. visible light or a portion thereof, say green light) will cause current of one polarity to be generated from one electrode (420) and the opposite polarity from the other electrode (420*a*), while a different predominant bandwidth of light (e.g. IR, or a different portion of visible light, say red light) shining on the MMRI-OPSISTER-D (401*a*) will cause current of reversed polarity to be generated from the electrodes (420 and 420*a*) (as compared to the electrodes 420 and 420*a* polarity from visible light stimulation in the first situation). Specifically, in typical illumination conditions, light composed of mixtures of different bandwidths will be found. Depending on the predominant bandwidth encountered, either the P+ or the N+ layer will receive greater light intensity, and be stimulated more intensely than the other, as a result. Therefore, one polarity of current will be generated from e.g. electrode (420) in one lighting condition predominant in one bandwidth, whereas a different polarity of current will be generated from electrode (420) in lighting conditions predominant in another bandwidth. In the orientation of the MMRI-OPSISTER-D (401*a*) of FIG. 27E within the subretinal space, light (430) is coming from the top. Electrode (420) is the stimulating electrode of the inner retina (66) as shown in FIG. 11 because it is in direct contact with that portion of the retina. The electrode (420*a*) which develops a opposite-polarity current to electrode (420) is facing away from the inner retina and serves as the electrical return of current from electrode (420). Because the MMRI-OPSISTER-D (401*a*) is a symmetric device, orientation of the MMRI-OPSISTER-D (401*a*) with either electrode (420) or electrode (420*a*) facing the inner retina and incoming light (430), produces the same stimulation polarity of the inner retina.

In typical patients with macular degeneration, for example, the light-sensing portion of the photoreceptor cell(s) is damaged or lost, leaving the remaining photoreceptor. When a device such as the MMRI-OPSISTER-D (401*a*) shown in FIG. 27E is placed into the subretinal space (82) of FIG. 11 in the same location as, but instead of the MMRI-4's (8), in contact with the remnant photoreceptor cells (64), and the appropriate bandwidth of light (e.g. visible light or a portion of that spectrum, say green light as discussed above) stimulates the N+ surface of the device facing incident light, the negative charges produced by the N+ surface of the device will induce a greater negativity in the internal portion of the remnant photoreceptor cells and create the sensation of light. In this example, the greater internal negativity in this location causes a signal representing light sensation to be transmitted to the bipolar cell responsible for transmitting the sensation of light.

Likewise, when a device such as the MMRI-OPSISTER-D (401*a*) shown in FIG. 27E is placed in the subretinal space (82) of FIG. 11 in the same location as, but instead of the MMRI-4's (8), in contact with the remnant photoreceptor cells (64), and the appropriate bandwidth of light (e.g. IR light or a different portion of the spectrum, say red light as discussed above) stimulates the P+ surface of the device facing incident light, the positive charges produced by the P+ surface of the device will induce a lesser negativity in the internal portion of the remnant photoreceptor cell and create the sensation of darkness or dark hues. In this example, the lesser internal negativity in this location will cause a signal representing a sensation of darkness or dark hues to be transmitted to the appropriate bipolar cell responsible for transmitting the sensation of darkness or dark hues.

The bridging electrodes (420, 420*a*) allows the P+ and N+ surfaces to electrically stimulate the retina through the same electrode. This is important to reduce the possibility of tissue injury due to prolonged exposure to currents that may flow in only one direction. However, it is believed that very little current is needed and will be induced to flow in the subretinal space by any of the devices disclosed herein. The provision of bridging electrodes (420, 420*a*) is done simply as a precaution. However, bridging electrodes also allow the MMRI-OPSISTER-D device to stimulate smaller areas of the retina, and therefore produce higher resolution, than other embodiments of this invention.

As shown in FIG. 27E, the MMRI-OPSISTER-D devices (401*a*) are typically on the order of 10 microns thick but may vary from 3 microns to 1000 microns in thickness. As shown in FIG. 28, the small silicon disc (405*a*) with its MMRI-OPSISTER-D devices (401*a*), shown implanted in the subretinal space (82), is typically on the order of 40 microns thick but may vary from 3 microns to 1000 microns in thickness.

We claim:

1. A retinal stimulation system comprising:
   a first light receiver for receipt of an ambient image;
   a light processor, coupled to the first light receiver, to provide image-based control based on the ambient image;

a light projector, coupled to the light processor, to provide light output based on the image-based control; and
retinal implant adapted to receive at least the light output.

2. The retinal stimulation system of claim 1, wherein the light output comprises diffuse infrared light.

3. The retinal stimulation system of claim 1, wherein the light output comprises ambient image-based infrared light.

4. The retinal stimulation system of claim 1, wherein the light output comprises ambient image-based visible light.

5. The retinal stimulation system of claim 1 wherein the retinal implant is adapted to receive the ambient image.

6. The retinal stimulation system of claim 1 wherein the retinal implant comprises at least one microphotodiode.

7. The retinal stimulation system of claim 6 wherein the at least one microphotodiode is adapted to stimulate a retina of an eye.

8. The retinal stimulation system of claim 1 wherein the light processor is adapted to control at least one of pulsing of the light output, intensity of the light output, duration of the light output and wavelength of the light output.

9. The retinal stimulation system of claim 1 further including a patient input device connected with the light processor.

10. The retinal stimulation system of claim 1 further including a pupil tracking device operably connected with the first light receiver to control an orientation of the first light receiver.

11. The retinal stimulation system of claim 10 wherein the first light receiver comprises a camera.

12. The retinal stimulation system of claim 1 further comprising a headset to accommodate at least the first light receiver and the light projector.

13. The retinal stimulation system of claim 12 wherein the headset comprises a glasses-like configuration.

14. The retinal stimulation system of claim 1 further including an optical element, operatively disposed between the light projector and the retinal implant, having an at least partially reflective surface.

15. The retinal stimulation system of claim 14 wherein the optical element comprises a substantially completely reflective mirror.

16. A retinal stimulation system comprising:
a headset;
a first light receiver coupled with the headset for receipt of an ambient image;
a light processor, coupled to the first light receiver, to provide image-based control based on the ambient image; and
a light projector, coupled to the light processor and headset, to provide light output based on the image-based control and configured to control operation of a retinal implant.

17. The retinal stimulation system of claim 16 further comprising the retinal implant adapted to receive at least the light output from the light projector.

18. The retinal stimulation system of claim 17 wherein the retinal implant comprises a microphotodiode.

19. The retinal stimulation system of claim 18 wherein the microphotodiode is adapted to stimulate a retina of an eye.

20. The retinal stimulation system of claim 16 further including a pupil tracking device operably connected with the first light receiver to control an orientation of the first light receiver.

21. The retinal stimulation system of claim 16 wherein the headset comprises a glasses-like configuration.

* * * * *